United States Patent
Keshavarz-Shokri et al.

(10) Patent No.: US 9,314,455 B2
(45) Date of Patent: Apr. 19, 2016

(54) SOLID FORMS OF 3-(6-(1-(2,2-DIFLUOROBENZO[D][1,3]DIOXOL-5-YL) CYCLOPROPANECARBOXAMIDO)-3-METHYLPYRIDIN-2-YL)BENZOIC ACID

(71) Applicant: VERTEX PHAMRACEUTICALS INCORPORATED, Boston, MA (US)

(72) Inventors: Ali Keshavarz-Shokri, San Diego, CA (US); Beili Zhang, San Diego, CA (US); Mariusz Krawiec, Marlborough, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 14/601,608

(22) Filed: Jan. 21, 2015

(65) Prior Publication Data

US 2015/0196539 A1   Jul. 16, 2015

Related U.S. Application Data

(60) Division of application No. 14/250,009, filed on Apr. 10, 2014, now Pat. No. 8,969,574, which is a continuation of application No. 13/940,361, filed on Jul. 12, 2013, now Pat. No. 8,742,122, which is a division of application No. 13/082,156, filed on Apr. 7, 2011, now Pat. No. 8,507,687.

(60) Provisional application No. 61/321,729, filed on Apr. 7, 2010.

(51) Int. Cl.
| | |
|---|---|
| A61K 31/44 | (2006.01) |
| C07D 405/00 | (2006.01) |
| A61K 31/443 | (2006.01) |
| C07D 213/75 | (2006.01) |
| C07D 405/12 | (2006.01) |
| C07D 405/14 | (2006.01) |
| A61K 31/47 | (2006.01) |
| A61K 45/06 | (2006.01) |
| C07D 407/12 | (2006.01) |

(52) U.S. Cl.
CPC .............. *A61K 31/443* (2013.01); *A61K 31/47* (2013.01); *A61K 45/06* (2013.01); *C07D 213/75* (2013.01); *C07D 405/12* (2013.01); *C07D 405/14* (2013.01); *C07D 407/12* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 6,426,331 | B1 | 7/2002 | McKinney et al. |
| 6,479,483 | B2 | 11/2002 | Bos et al. |
| 6,770,637 | B2 | 8/2004 | Godel et al. |
| 7,407,976 | B2 | 8/2008 | Miller et al. |
| 7,495,103 | B2 | 2/2009 | Hadida Ruah et al. |
| 7,553,855 | B2 | 6/2009 | Young et al. |
| 7,598,412 | B2 | 10/2009 | Hadida Ruah et al. |
| 7,645,789 | B2 | 1/2010 | Hadida Ruah et al. |
| 7,659,268 | B2 | 2/2010 | Hadida Ruah et al. |
| 7,671,221 | B2 | 3/2010 | Hadida Ruah et al. |
| 7,691,902 | B2 | 4/2010 | Hadida Ruah et al. |
| 7,741,321 | B2 | 6/2010 | Hadida Ruah et al. |
| 7,754,739 | B2 | 7/2010 | Hadida Ruah et al. |
| 7,776,905 | B2 | 8/2010 | Hadida Ruah et al. |
| 7,846,951 | B2 | 12/2010 | Miller et al. |
| 7,893,094 | B2 | 2/2011 | Pollard et al. |
| 7,956,052 | B2 | 6/2011 | Hadida Ruah et al. |
| 7,973,038 | B2 | 7/2011 | Hadida Ruah et al. |
| 7,973,169 | B2 | 7/2011 | Hadida Ruah et al. |
| 7,977,322 | B2 | 7/2011 | Ruah et al. |
| 7,999,113 | B2 | 8/2011 | Hadida-Ruah et al. |
| 8,012,999 | B2 | 9/2011 | Hadida Ruah et al. |
| 8,039,491 | B2 | 10/2011 | Hadida Ruah et al. |
| 8,076,357 | B2 | 12/2011 | Young et al. |
| 8,101,767 | B2 | 1/2012 | Ruah et al. |
| 8,124,781 | B2 | 2/2012 | Siesel |
| 8,163,772 | B2 | 4/2012 | DeMattei et al. |
| 8,188,283 | B2 | 5/2012 | Binch et al. |
| 8,227,615 | B2 | 7/2012 | Hadida Ruah et al. |
| 8,232,302 | B2 | 7/2012 | Miller et al. |
| 8,242,149 | B2 | 8/2012 | Ruah et al. |
| 8,299,099 | B2 | 10/2012 | Ruah et al. |
| 8,314,239 | B2 | 11/2012 | Binch et al. |
| 8,314,256 | B2 | 11/2012 | Ruah et al. |
| 8,318,733 | B2 | 11/2012 | Hadida Ruah et al. |
| 8,324,207 | B2 | 12/2012 | Hadida-Ruah et al. |

(Continued)

FOREIGN PATENT DOCUMENTS

| | | |
|---|---|---|
| WO | 2007056341 | 5/2007 |
| WO | 2007075946 | 7/2007 |

(Continued)

OTHER PUBLICATIONS

Bhattacharya excerpt from Brittain, H. ed., Polymorphism in Pharmaceutical Solids Drugs and the Pharmaceutical Sciences: vol. 95, New York Marcel Dekker, Inc., 1999.

(Continued)

*Primary Examiner* — Heidi Reese

(74) *Attorney, Agent, or Firm* — Finnegan, Henderson, Farabow, Garrett & Dunner, LLP

(57) ABSTRACT

The present invention relates to a substantially a solid form of 3-(6-(1-(2,2-difluorobenzo[d][1,3]dioxol-5-yl)cyclopropanecarboxamido)-3-methylpyridin-2-yl)benzoic acid (Compound 1, Solvate Form A and Compound 1, HCl Salt Form A), processes for making such forms, pharmaceutical compositions thereof, and methods of treatment therewith.

37 Claims, 23 Drawing Sheets

(56) References Cited

U.S. PATENT DOCUMENTS

| | | |
|---|---|---|
| 8,324,242 B2 | 12/2012 | Ruah et al. |
| 8,344,147 B2 | 1/2013 | Ambhaikar et al. |
| 8,354,427 B2 | 1/2013 | Van Goor et al. |
| 8,362,253 B2 | 1/2013 | DeMattei et al. |
| 8,367,660 B2 | 2/2013 | Binch et al. |
| 8,389,727 B2 | 3/2013 | Zhang et al. |
| 8,399,479 B2 | 3/2013 | Binch et al. |
| 8,404,849 B2 | 3/2013 | Sun et al. |
| 8,404,865 B2 | 3/2013 | Ambhaikar et al. |
| 8,410,132 B2 | 4/2013 | Binch et al. |
| 8,410,274 B2 | 4/2013 | Hurter et al. |
| 8,415,387 B2 | 4/2013 | Ruah et al. |
| 8,431,605 B2 | 4/2013 | Hadida Ruah et al. |
| 8,436,014 B2 | 5/2013 | Zhang et al. |
| 8,461,156 B2 | 6/2013 | Hadida Ruah et al. |
| 8,461,342 B2 | 6/2013 | Siesel |
| 8,461,352 B2 | 6/2013 | Ambhaikar et al. |
| 8,471,029 B2 | 6/2013 | Arekar et al. |
| 8,476,442 B2 | 7/2013 | DeMattei et al. |
| 8,507,524 B2 | 8/2013 | Ruah et al. |
| 8,507,534 B2 | 8/2013 | Keshavarz-Shokri et al. |
| 8,507,687 B2 | 8/2013 | Keshavarz-Shokri et al. |
| 8,513,282 B2 | 8/2013 | Binch et al. |
| 8,524,767 B2 | 9/2013 | Hadida Ruah et al. |
| 8,524,910 B2 | 9/2013 | Hadida Ruah et al. |
| 8,541,453 B2 | 9/2013 | Hadida-Ruah et al. |
| 8,552,006 B2 | 10/2013 | Binch et al. |
| 8,552,034 B2 | 10/2013 | Verwijs et al. |
| 8,563,573 B2 | 10/2013 | Ruah et al. |
| 8,563,593 B2 | 10/2013 | Alargova et al. |
| 8,575,209 B2 | 11/2013 | Ruah et al. |
| 8,586,615 B2 | 11/2013 | Hadida-Ruah et al. |
| 8,592,602 B2 | 11/2013 | Siesel et al. |
| 8,598,181 B2 | 12/2013 | Hadida Ruah et al. |
| 8,598,205 B2 | 12/2013 | Binch et al. |
| 8,604,203 B2 | 12/2013 | Binch et al. |
| 8,609,703 B2 | 12/2013 | Ruah et al. |
| 8,614,325 B2 | 12/2013 | Yang et al. |
| 8,614,327 B2 | 12/2013 | Sheth et al. |
| 8,623,894 B2 | 1/2014 | DeMattei et al. |
| 8,623,905 B2 | 1/2014 | Ruah et al. |
| 8,629,162 B2 | 1/2014 | Hadida-Ruah et al. |
| 8,633,189 B2 | 1/2014 | Binch et al. |
| 8,642,609 B2 | 2/2014 | Makings et al. |
| 8,653,103 B2 | 2/2014 | Keshavarz-Shokri et al. |
| 8,674,108 B2 | 3/2014 | Luisi et al. |
| 8,710,075 B2 | 4/2014 | Binch et al. |
| 8,716,338 B2 | 5/2014 | Young et al. |
| 8,722,704 B2 | 5/2014 | Hadida Ruah et al. |
| 8,741,922 B2 | 6/2014 | Zhang et al. |
| 8,741,925 B2 | 6/2014 | Hadida-Ruah et al. |
| 8,741,933 B2 | 6/2014 | Hadida Ruah et al. |
| 8,741,939 B2 | 6/2014 | Hadida Ruah et al. |
| 8,742,122 B2 | 6/2014 | Keshavarz-Shokri et al. |
| 8,748,612 B2 | 6/2014 | Binch et al. |
| 8,754,222 B2 | 6/2014 | Ambhaikar et al. |
| 8,754,224 B2 | 6/2014 | Hurter et al. |
| 8,759,335 B2 | 6/2014 | Hadida Ruah et al. |
| 8,765,957 B2 | 7/2014 | DeMattei et al. |
| 8,785,476 B2 | 7/2014 | Arekar et al. |
| 8,785,640 B2 | 7/2014 | Binch et al. |
| 8,796,308 B2 | 8/2014 | Yang et al. |
| 8,796,312 B2 | 8/2014 | Hadida Ruah et al. |
| 8,802,700 B2 | 8/2014 | Sheth et al. |
| 8,802,844 B2 | 8/2014 | Gallardo-Godoy et al. |
| 8,802,868 B2 | 8/2014 | Keshavarz-Shokri et al. |
| 8,816,093 B2 | 8/2014 | Siesel et al. |
| 8,822,451 B2 | 9/2014 | Ruah et al. |
| 8,829,204 B2 | 9/2014 | Hadida Ruah et al. |
| 8,835,639 B2 | 9/2014 | DeMattei et al. |
| 8,846,718 B2 | 9/2014 | Keshavarz-Shokri et al. |
| 8,846,753 B2 | 9/2014 | Hadida Ruah et al. |
| 8,853,254 B2 | 10/2014 | Hadida Ruah et al. |
| 8,853,415 B2 | 10/2014 | Hadida Ruah et al. |
| 8,883,206 B2 | 11/2014 | Dokou et al. |
| 8,884,018 B2 | 11/2014 | Ambhaikar et al. |
| 8,889,875 B2 | 11/2014 | Ruah et al. |
| 8,912,199 B2 | 12/2014 | Hadida Ruah et al. |
| 8,952,049 B2 | 2/2015 | Ruah et al. |
| 8,952,050 B2 | 2/2015 | Ruah et al. |
| 8,962,856 B2 | 2/2015 | Hadida Ruah et al. |
| 8,969,382 B2 | 3/2015 | Binch et al. |
| 8,969,386 B2 | 3/2015 | Hadida Ruah et al. |
| 8,969,574 B2 | 3/2015 | Keshavarz-Shokri et al. |
| 8,993,600 B2 | 3/2015 | Hadida Ruah et al. |
| 8,999,976 B2 | 4/2015 | Binch et al. |
| 9,012,473 B2 | 4/2015 | Hadida Ruah et al. |
| 9,012,496 B2 | 4/2015 | Alargova et al. |
| 9,012,652 B2 | 4/2015 | Siesel |
| 9,035,072 B2 | 5/2015 | Belmont et al. |
| 9,045,425 B2 | 6/2015 | Luisi et al. |
| 9,051,303 B2 | 6/2015 | Keshavarz-Shokri et al. |
| 9,051,324 B2 | 6/2015 | Binch et al. |
| 9,079,916 B2 | 7/2015 | Hadida Ruah et al. |
| 2003/0125315 A1 | 7/2003 | Mjalli et al. |
| 2005/0059687 A1 | 3/2005 | Makings et al. |
| 2005/0070718 A1 | 3/2005 | Lubisch et al. |
| 2005/0113423 A1 | 5/2005 | Van Goor et al. |
| 2005/0130970 A1 | 6/2005 | Miller et al. |
| 2005/0148648 A1 | 7/2005 | Hadida Ruah et al. |
| 2005/0176789 A1 | 8/2005 | Hadida Ruah et al. |
| 2006/0052358 A1 | 3/2006 | Ruah et al. |
| 2006/0074075 A1 | 4/2006 | Hadida Ruah et al. |
| 2006/0217448 A1 | 9/2006 | Kelly et al. |
| 2007/0105833 A1 | 5/2007 | Ruah et al. |
| 2007/0238775 A1 | 10/2007 | Ruah et al. |
| 2007/0244159 A1 | 10/2007 | Hadida Ruah et al. |
| 2007/0264196 A1 | 11/2007 | Ruah et al. |
| 2008/0009524 A1 | 1/2008 | Hadida Ruah et al. |
| 2008/0019915 A1 | 1/2008 | Hadida Ruah et al. |
| 2008/0044355 A1 | 2/2008 | Ruah et al. |
| 2008/0071095 A1 | 3/2008 | Hadida Ruah et al. |
| 2008/0090864 A1 | 4/2008 | Young et al. |
| 2008/0113985 A1 | 5/2008 | Ruah et al. |
| 2008/0161371 A1 | 7/2008 | Hadida Ruah et al. |
| 2008/0176899 A1 | 7/2008 | Ruah et al. |
| 2008/0286204 A1 | 11/2008 | Hadida Ruah et al. |
| 2008/0306062 A1 | 12/2008 | Hadida Ruah et al. |
| 2009/0018140 A1 | 1/2009 | Miller et al. |
| 2009/0099230 A1 | 4/2009 | De Mattei et al. |
| 2009/0105272 A1 | 4/2009 | Grootenhuis et al. |
| 2009/0131492 A1 | 5/2009 | Ruah et al. |
| 2009/0143381 A1 | 6/2009 | Hadida Ruah et al. |
| 2009/0170905 A1 | 7/2009 | Keshavarz-Shokri et al. |
| 2009/0176839 A1 | 7/2009 | Keshavarz-Shokri et al. |
| 2009/0176989 A1 | 7/2009 | Siesel et al. |
| 2009/0221597 A1 | 9/2009 | Ruah et al. |
| 2009/0227797 A1 | 9/2009 | Hadida Ruah et al. |
| 2009/0246137 A1 | 10/2009 | Hadida Ruah et al. |
| 2009/0246820 A1 | 10/2009 | Singh et al. |
| 2009/0253736 A1 | 10/2009 | Hadida Ruah et al. |
| 2009/0298876 A1 | 12/2009 | Hadida Ruah et al. |
| 2010/0036130 A1 | 2/2010 | Siesel et al. |
| 2010/0069434 A1 | 3/2010 | Young et al. |
| 2010/0074949 A1 | 3/2010 | Rowe et al. |
| 2010/0125090 A1 | 5/2010 | Hadida Ruah et al. |
| 2010/0144798 A1 | 6/2010 | VanGoor et al. |
| 2010/0256184 A1 | 10/2010 | Rowe et al. |
| 2011/0064811 A1 | 3/2011 | Hurter et al. |
| 2011/0098311 A1 | 4/2011 | Van Goor et al. |
| 2011/0177999 A1 | 7/2011 | Singh et al. |
| 2011/0251253 A1 | 10/2011 | Keshavarz-Shokri et al. |
| 2011/0257223 A1 | 10/2011 | Goor et al. |
| 2011/0288122 A1 | 11/2011 | Van Goor et al. |
| 2012/0035179 A1 | 2/2012 | Hadida Ruah et al. |
| 2012/0046330 A1 | 2/2012 | Alargova et al. |
| 2012/0064157 A1 | 3/2012 | Dokou et al. |
| 2012/0122921 A1 | 5/2012 | DeMallei et al. |
| 2012/0122922 A1 | 5/2012 | Young et al. |
| 2012/0184583 A1 | 7/2012 | Van Goor et al. |
| 2012/0220625 A1 | 8/2012 | Rowe et al. |
| 2012/0232059 A1 | 9/2012 | Hadida Ruah et al. |
| 2012/0258983 A1 | 10/2012 | Rowe et al. |
| 2013/0012536 A1 | 1/2013 | Hadida Ruah et al. |

(56) References Cited

U.S. PATENT DOCUMENTS

| | | |
|---|---|---|
| 2013/0018071 A1 | 1/2013 | Arekar et al. |
| 2013/0085158 A1 | 4/2013 | Keshavarz-Shokri et al. |
| 2013/0090354 A1 | 4/2013 | Van Goor et al. |
| 2013/0095181 A1 | 4/2013 | Verwijs et al. |
| 2013/0116238 A1 | 5/2013 | Looker et al. |
| 2013/0131107 A1 | 5/2013 | Van Goor et al. |
| 2013/0143919 A1 | 6/2013 | Van Goor et al. |
| 2013/0158071 A1 | 6/2013 | Van Goor et al. |
| 2013/0186801 A1 | 7/2013 | Verwijs et al. |
| 2013/0224293 A1 | 8/2013 | Dokou et al. |
| 2013/0231368 A1 | 9/2013 | Zhang et al. |
| 2013/0237569 A1 | 9/2013 | Hadida Ruah et al. |
| 2013/0245010 A1 | 9/2013 | Hadida Ruah et al. |
| 2013/0245011 A1 | 9/2013 | Hadida Ruah et al. |
| 2013/0303484 A1 | 11/2013 | Grootenhuis et al. |
| 2013/0331567 A1 | 12/2013 | Hadida Ruah et al. |
| 2014/0023706 A1 | 1/2014 | Verwijs et al. |
| 2014/0024672 A1 | 1/2014 | Hadida-Ruah et al. |
| 2014/0080825 A1 | 3/2014 | Hadida-Ruah et al. |
| 2014/0094499 A1 | 4/2014 | Alargova et al. |
| 2014/0112988 A1 | 4/2014 | Rowe et al. |
| 2014/0121208 A1 | 5/2014 | Van Goor et al. |
| 2014/0121379 A1 | 5/2014 | Siesel et al. |
| 2014/0142138 A1 | 5/2014 | Van Goor et al. |
| 2014/0155431 A1 | 6/2014 | Hadida-Ruah et al. |
| 2014/0155626 A1 | 6/2014 | Hadida-Ruah et al. |
| 2014/0163011 A1 | 6/2014 | Hadida-Ruah et al. |
| 2014/0163068 A1 | 6/2014 | Verwijs et al. |
| 2014/0206720 A1 | 7/2014 | Young et al. |
| 2014/0221424 A1 | 8/2014 | Zha et al. |
| 2014/0235668 A1 | 8/2014 | Binch et al. |
| 2014/0242172 A1 | 8/2014 | Hurter et al. |
| 2014/0243289 A1 | 8/2014 | Grootenhuis et al. |
| 2014/0256770 A1 | 9/2014 | DeMattei et al. |
| 2014/0303204 A1 | 10/2014 | Binch et al. |
| 2014/0303205 A1 | 10/2014 | Yang et al. |
| 2014/0315948 A1 | 10/2014 | Rowe et al. |
| 2014/0323521 A1 | 10/2014 | Van Goor et al. |
| 2014/0329855 A1 | 11/2014 | Arekar et al. |
| 2014/0336393 A1 | 11/2014 | Ambhaikar et al. |
| 2014/0343098 A1 | 11/2014 | Sheth et al. |
| 2014/0343315 A1 | 11/2014 | Hadida Ruah et al. |
| 2014/0350281 A1 | 11/2014 | DeMattei et al. |
| 2014/0371275 A1 | 12/2014 | Keshavarz-Shokri et al. |
| 2015/0010628 A1 | 1/2015 | Dokou et al. |
| 2015/0024047 A1 | 1/2015 | Dokou et al. |
| 2015/0025076 A1 | 1/2015 | Hadida Ruah et al. |
| 2015/0031720 A1 | 1/2015 | Gallardo-Godoy |
| 2015/0031722 A1 | 1/2015 | Hadida Ruah et al. |
| 2015/0065487 A1 | 3/2015 | Hadida-Ruah et al. |
| 2015/0065497 A1 | 3/2015 | Hadida-Ruah et al. |
| 2015/0065500 A1 | 3/2015 | Hadida-Ruah et al. |
| 2015/0080431 A1 | 3/2015 | Van Goor et al. |
| 2015/0094304 A1 | 4/2015 | Ruah et al. |
| 2015/0119441 A1 | 4/2015 | Hadida Ruah |
| 2015/0126566 A1 | 5/2015 | Hadida-Ruah |
| 2015/0140094 A1 | 5/2015 | Verwijs et al. |
| 2015/0141459 A1 | 5/2015 | Van Goor et al. |
| 2015/0164881 A1 | 6/2015 | Van Goor |
| 2015/0164883 A1 | 6/2015 | Van Goor |
| 2015/0166516 A1 | 6/2015 | Hadida-Ruah et al. |
| 2015/0174098 A1 | 6/2015 | Ruah et al. |
| 2015/0182517 A1 | 7/2015 | Alargova et al. |
| 2015/0190390 A1 | 7/2015 | Hadida Ruah et al. |

FOREIGN PATENT DOCUMENTS

| | | |
|---|---|---|
| WO | 2008127399 | 10/2008 |
| WO | 2008147952 | 12/2008 |
| WO | 2009006315 | 1/2009 |
| WO | 2009023509 | 2/2009 |
| WO | 2009036412 | 3/2009 |
| WO | 2009038913 | 3/2009 |
| WO | 2009073757 | 6/2009 |
| WO | 2009076593 | 6/2009 |
| WO | 2010037066 | 4/2010 |

OTHER PUBLICATIONS

Braga, D., et al., Struct. Bond 2009, vol. 132.
International Search Report of PCT/US2011/031588, mailed Dec. 16, 2011.
Notice of Allowance mailed May 28, 2015, in U.S. Appl. No. 13/672,538.
Notice of Allowance mailed May 28, 2015, in U.S. Appl. No. 14/470,836.
U.S. Appl. No. 14/676,205, filed Apr. 1, 2015.
U.S. Appl. No. 14/686,117, filed Apr. 14, 2015.
U.S. Appl. No. 14/687,286, filed Apr. 15, 2015.
U.S. Appl. No. 14/689,391, filed Apr. 17, 2015.
U.S. Appl. No. 14/689,860, filed Apr. 17, 2015.
U.S. Appl. No. 14/715,682, filed May 19, 2015.
U.S. Appl. No. 14/730,726, filed Jun. 4, 2015.

SOLID FORMS OF 3-(6-(1-(2,2-DIFLUOROBENZO[D][1,3]DIOXOL-5-YL)CYCLOPROPANECARBOXAMIDO)-3-METHYLPYRIDIN-2-YL)BENZOIC ACID

CROSS-REFERENCE TO RELATED APPLICATIONS

The present application claims the benefit of priority under 35 U.S.C. §119 to U.S. Provisional Application Ser. No. 61/321,729, filed Apr. 7, 2010, and entitled "Solid Forms of 3-(6-(1-(2,2-Difluorobenzo[d][1,3]dioxol-5-yl)cyclopropanecarboxamido)-3-methyl pyridin-2-yl)benzoic acid," the entire contents of which is incorporated herein by reference.

TECHNICAL FIELD OF THE INVENTION

The present invention relates to solid state forms, for example, crystalline forms, of the compound 3-(6-(1-(2,2-difluorobenzo[d][1,3]dioxol-5-yl)cyclopropanecarboxamido)-3-methylpyridin-2-yl)benzoic acid, pharmaceutical compositions thereof, and methods therewith.

BACKGROUND OF THE INVENTION

CFTR is a cAMP/ATP-mediated anion channel that is expressed in a variety of cell types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See, Gregory, R. J., et al. (1990) Nature 347:382-386; Rich, D. P., et al. (1990) Nature 347:358-362), (Riordan, J. R., et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia lead to reduced apical anion secretion, which causes an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile, and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease-causing mutations (Cutting, G. R., et al. (1990) Nature 346:366-369; Dean, M., et al. (1990) Cell 61:863:870; and Kerem, B-S., et al. (1989) Science 245:1073-1080; Kerem, B-S et al. (1990) Proc. Natl. Acad. Sci. USA 87:8447-8451). To date, more than 1000 disease-causing mutations in the CF gene have been identified. The most prevalent mutation is a deletion of phenylalanine at position 508 of the CFTR amino acid sequence, and is commonly referred to as ΔF508-CFTR. This mutation occurs in approximately 70 percent of the cases of cystic fibrosis and is associated with a severe disease.

The deletion of residue 508 in ΔF508-CFTR prevents the nascent protein from folding correctly. This results in the inability of the mutant protein to exit the endoplasmic reticulum (ER), and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia, leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR also transports a variety of molecules, it is clear that the transport of anions represents one element in an important mechanism of transporting ions and water across the epithelium. The other elements include the epithelial Na$^+$ channel, ENaC, Na$^+$/2Cl$^-$/K$^+$ co-transporter, Na$^+$—K$^+$-ATPase pump, and the basolateral membrane K$^+$ channels that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the Na$^+$—K$^+$-ATPase pump and Cl$^-$ channels expressed on the basolateral surface of the cell. Secondary active transport of chloride from the luminal side leads to the accumulation of intracellular chloride, which can then passively leave the cell via Cl$^-$ channels, resulting in a vectorial transport. Arrangement of Na$^+$/2Cl$^-$/K$^+$ co-transporter, Na$^+$—K$^+$-ATPase pump, and the basolateral membrane K$^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective endoplasmic reticulum (ER) processing of ABC transporters by the ER machinery has been shown to be the underlying basis not only for CF disease, but for a wide range of other isolated and inherited diseases. The two ways that the ER machinery can malfunction are either by loss of coupling to ER export of the proteins leading to degradation or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)].

The compound 3-(6-(1-(2,2-difluorobenzo[d][1,3]dioxol-5-yl)cyclopropane carboxamido)-3-methylpyridin-2-yl)benzoic acid in salt form is disclosed in International PCT Publication WO 2007056341 (said publication being incorporated herein by reference in its entirety) as a modulator of CFTR activity and thus as a useful treatment for CFTR-mediated diseases such as cystic fibrosis. Form I of 3-(6-(1-(2,2-difluorobenzo[d][1,3]dioxol-5-yl)cyclopropanecarboxamido)-3-methylpyridin-2-yl)benzoic acid ("Compound 1, Form I"), which is a substantially crystalline and salt-free form, is disclosed in U.S. patent application Ser. No. 12/327,902, filed Dec. 4, 2008, incorporated by reference herein in its entirety. A need remains, however, for other stable solid forms of said compound that can be used readily in pharmaceutical compositions suitable for use as therapeutics.

SUMMARY OF THE INVENTION

The present invention relates to solid polymorphic forms of the compound 3-(6-(1-(2,2-difluorobenzo[d][1,3]dioxol-5-yl)cyclopropanecarboxamido)-3-methylpyridin-2-yl)benzoic acid (hereinafter "Compound 1") which has the structure below:

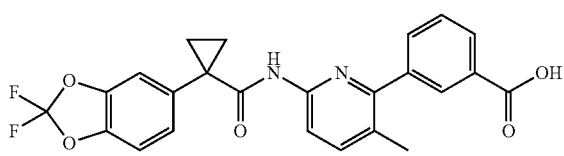

Polymorphism is a known phenomena for solid forms of compounds. The physical characteristics of polymorphs are known to affect, for example, solubility, rate of dissolution, flow properties, rate of absorption, and stability. Hence, choice of a particular polymorph is important in the development and preparation of compositions.

In one embodiment, Compound 1 is in solvated form, designated herein as "Compound 1, Solvate Form A." In one embodiment, the solvate form is Compound 1, Methanol Solvate Form A. In another embodiment, the solvate is Compound 1, Ethanol Solvate Form A. Other embodiments include:
  Compound 1, Acetone Solvate Form A;
  Compound 1, 2-Propanol Solvate Form A;
  Compound 1, Acetonitrile Solvate Form A;
  Compound 1, Tetrahydrofuran Solvate Form A;
  Compound 1, Methyl Acetate Solvate Form A;
  Compound 1, 2-Butanone Solvate Form A;
  Compound 1, Ethyl Formate Solvate Form A; and
  Compound 1, 2-Methyltetrahydrofuran Solvate Form A.

In still another aspect, Compound 1 is in a salt form. The salt form is referred to as "Compound 1, HCl Salt Form A".

The Compound 1 solid forms disclosed herein and pharmaceutical compositions thereof are useful for lessening the severity of CFTR-mediated diseases such as, for example, cystic fibrosis. The Compound 1 solid forms can be used to prepare other Compound 1 solid forms, as well as pharmaceutical compositions comprising Compound 1 solid forms, using the processes disclosed herein.

DETAILED DESCRIPTION OF THE INVENTION

Definitions

Figure 1:
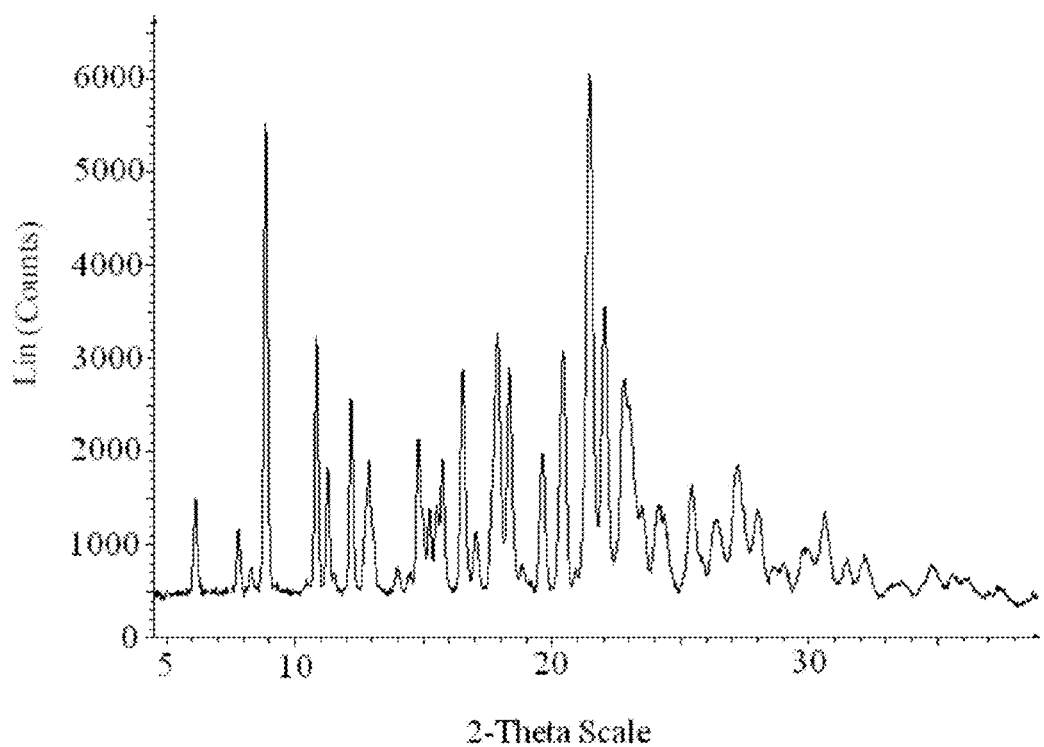
FIG. 1 is an X-ray powder diffraction pattern of Compound 1, Solvate Form A.

As used herein, the following definitions shall apply unless otherwise indicated.

The term "CFTR" as used herein means cystic fibrosis transmembrane conductance regulator or a mutation thereof capable of regulator activity, including, but not limited to, ΔF508 CFTR and G551D CFTR (see, e.g., http://www.genet.sickkids.on.ca/cftr/ last visited May 28, 2009, for CFTR mutations).

As used herein, "crystalline" refers to compounds or compositions where the structural units are arranged in fixed geometric patterns or lattices, so that crystalline solids have rigid long range order. The structural units that constitute the crystal structure can be atoms, molecules, or ions. Crystalline solids show definite melting points.

As used herein, the term "substantially crystalline" refers to a solid material having predominantly long range order in the position of its molecules. For example, substantially crystalline materials have more than about 85% crystallinity (e.g., more than about 90% crystallinity or more than about 95% crystallinity). It is also noted that the term 'substantially crystalline' includes the descriptor 'crystalline,' which refers to materials having 100% crystallinity.

As used herein, the term "modulating" means increasing or decreasing, e.g. activity, by a measurable amount.

As used herein, "isostructural solvate" refers to a compound crystalline lattice having a plurality of repeating cavities wherein some or all of the cavities may optionally be occupied by a solvent molecule which is the same or different.

The term "DSC" means differential scanning calorimetry.

The term "TGA" means thermogravimetric analysis.

Compound 1, Solvate Form A

In one aspect, the invention features a Compound 1 solid form which is an isostructural solvate form, referred to as "Compound 1, Solvate Form A."

Compound 1, Solvate Form A, as disclosed herein, comprises a crystalline lattice of Compound 1 in which voids in the crystalline lattice are empty, or occupied, or partially occupied by one or more molecules of a suitable solvent. Suitable solvents include, but are not limited to, methanol, ethanol, acetone, 2-propanol, acetonitrile, tetrahydrofuran, methyl acetate, 2-butanone, ethyl formate, and 2-methyl tetrahydrofuran. Certain physical characteristics of Compound 1 isostructural solvate forms, such as X-ray powder diffraction, melting point, and DSC, are not substantially affected by the particular solvent molecule in question.

In one embodiment, Compound 1, Solvate Form A is characterized by one or more peaks at 21.50 to 21.90 degrees, 8.80 to 9.20 degrees, and 10.80 to 11.20 degrees in an X-ray powder diffraction obtained using Cu K alpha radiation.

In another embodiment, Compound 1, Solvate Form A is characterized by one or more peaks at 21.50 to 21.90 degrees, 8.80 to 9.20 degrees, 10.80 to 11.20 degrees, 18.00 to 18.40 degrees, and 22.90 to 23.30 degrees in an X-ray powder diffraction obtained using Cu K alpha radiation.

In another embodiment, Compound 1, Solvate Form A is characterized by one or more peaks at 21.70, 8.98, and 11.04 degrees.

In another embodiment, Compound 1, Solvate Form A is characterized by one or more peaks at 21.70, 8.98, 11.04, 18.16, and 23.06 degrees.

In another embodiment, Compound 1, Solvate Form A is characterized by a peak at 21.50 to 21.90 degrees.

In another embodiment, Compound 1, Solvate Form A is further characterized by a peak at 21.70 degrees.

In another embodiment, Compound 1, Solvate Form A is further characterized by a peak at 8.80 to 9.20 degrees.

In another embodiment, Compound 1, Solvate Form A is further characterized by a peak at 8.98 degrees.

In another embodiment, Compound 1, Solvate Form A is further characterized by a peak at 10.80 to 11.20 degrees.

In another embodiment, Compound 1, Solvate Form A is further characterized by a peak at 11.04.

In another embodiment, Compound 1, Solvate Form A is further characterized by a peak at 18.00 to 18.40 degrees.

In another embodiment, Compound 1, Solvate Form A is further characterized by a peak at 18.16 degrees.

In another embodiment, Compound 1, Solvate Form A is further characterized by a peak at 22.90 to 23.30 degrees.

In another embodiment, Compound 1, Solvate Form A is further characterized by a peak at 23.06 degrees.

In another embodiment, Compound 1, Solvate Form A is further characterized by a peak at 20.40 to 20.80 degrees.

In another embodiment, Compound 1, Solvate Form A is further characterized by a peak at 20.63 degrees.

In another embodiment, Compound 1, Solvate Form A is further characterized by a peak at 22.00 to 22.40 degrees.

In another embodiment, Compound 1, Solvate Form A is further characterized by a peak at 22.22 degrees.

In another embodiment, Compound 1, Solvate Form A is further characterized by a peak at 18.40 to 18.80 degrees.

In another embodiment, Compound 1, Solvate Form A is further characterized by a peak at 18.57 degrees.

In another embodiment, Compound 1, Solvate Form A is further characterized by a peak at 16.50 to 16.90 degrees.

In another embodiment, Compound 1, Solvate Form A is further characterized by a peak at 16.66 degrees.

In another embodiment, Compound 1, Solvate Form A is further characterized by a peak at 19.70 to 20.10 degrees.

In another embodiment, Compound 1, Solvate Form A is further characterized by a peak at 19.86 degrees.

In some embodiments, Compound 1, Solvate Form A is characterized by a diffraction pattern substantially similar to that of FIG. 1.

Figure 2:
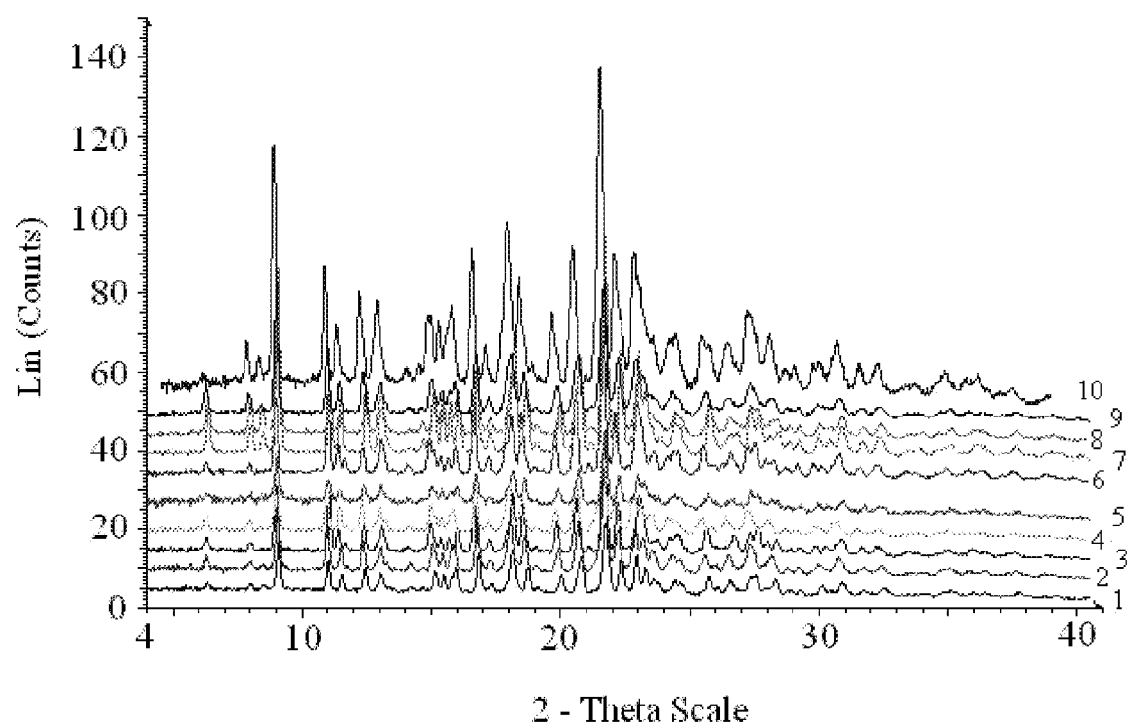
FIG. 2 provides X-ray diffraction patterns of Compound 1, Solvate Forms selected from:
  1) Compound 1, Methanol Solvate Form A;
  2) Compound 1, Ethanol Solvate Form A;
  3) Compound 1, Acetone Solvate Form A;
  4) Compound 1, 2-Propanol Solvate Form A;
  5) Compound 1, Acetonitrile Solvate Form A;
  6) Compound 1, Tetrahydrofuran Solvate Form A;
  7) Compound 1, Methyl Acetate Solvate Form A;
  8) Compound 1, 2-Butanone Solvate Form A;
  9) Compound 1, Ethyl Formate Solvate Form A; and
  10) Compound 1, 2-Methyltetrahydrofuran Solvate Form A.

In some embodiments, Compound 1, Solvate Form A is characterized by diffraction patterns substantially similar to those provided in FIG. 2.

In other embodiments, the solvate or solvate mixture that forms Solvate Form A with Compound 1 is selected from the group consisting of an organic solvent of sufficient size to fit in the voids in the crystalline lattice of Compound 1. In some embodiments, the solvate is of sufficient size to fit in voids measuring about 100 Å$^3$.

Figure 3:
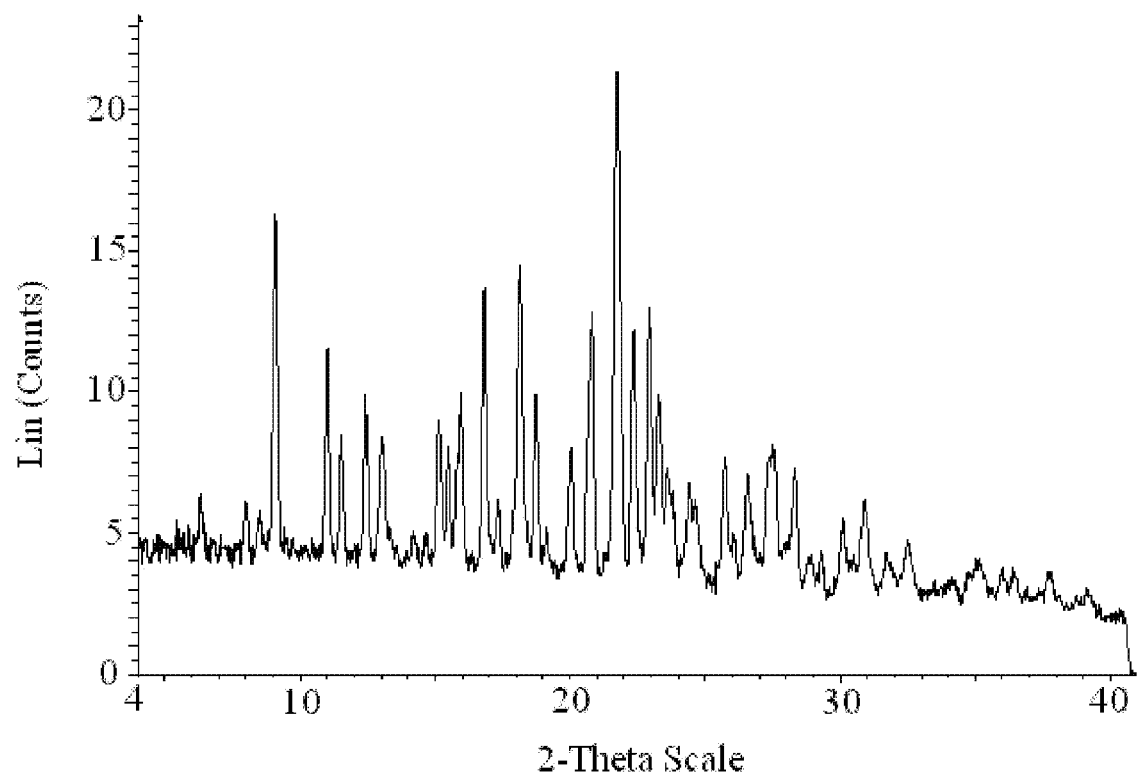
FIG. 3 provides an X-ray diffraction pattern of Compound 1, Methanol Solvate Form A.
Figure 4:
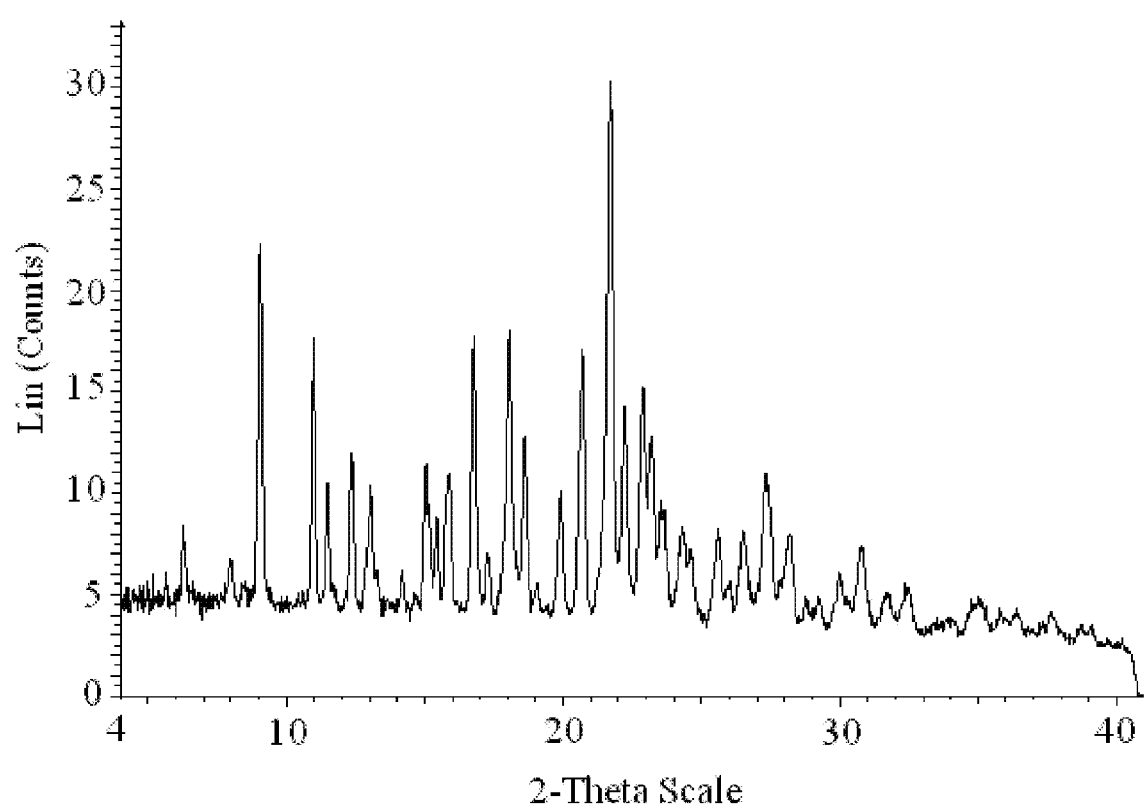
FIG. 4 provides an X-ray diffraction pattern of Compound 1, Ethanol Solvate Form A.
Figure 5:
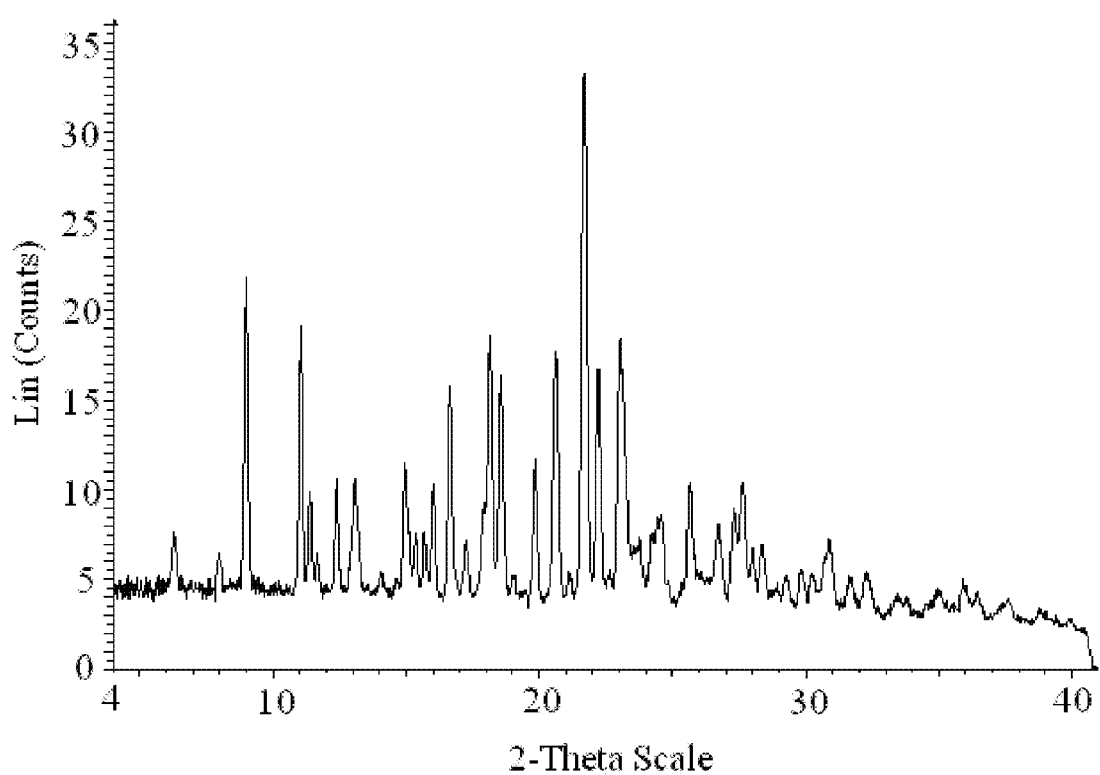
FIG. 5 provides an X-ray diffraction pattern of Compound 1, Acetone Solvate Form A.
Figure 6:
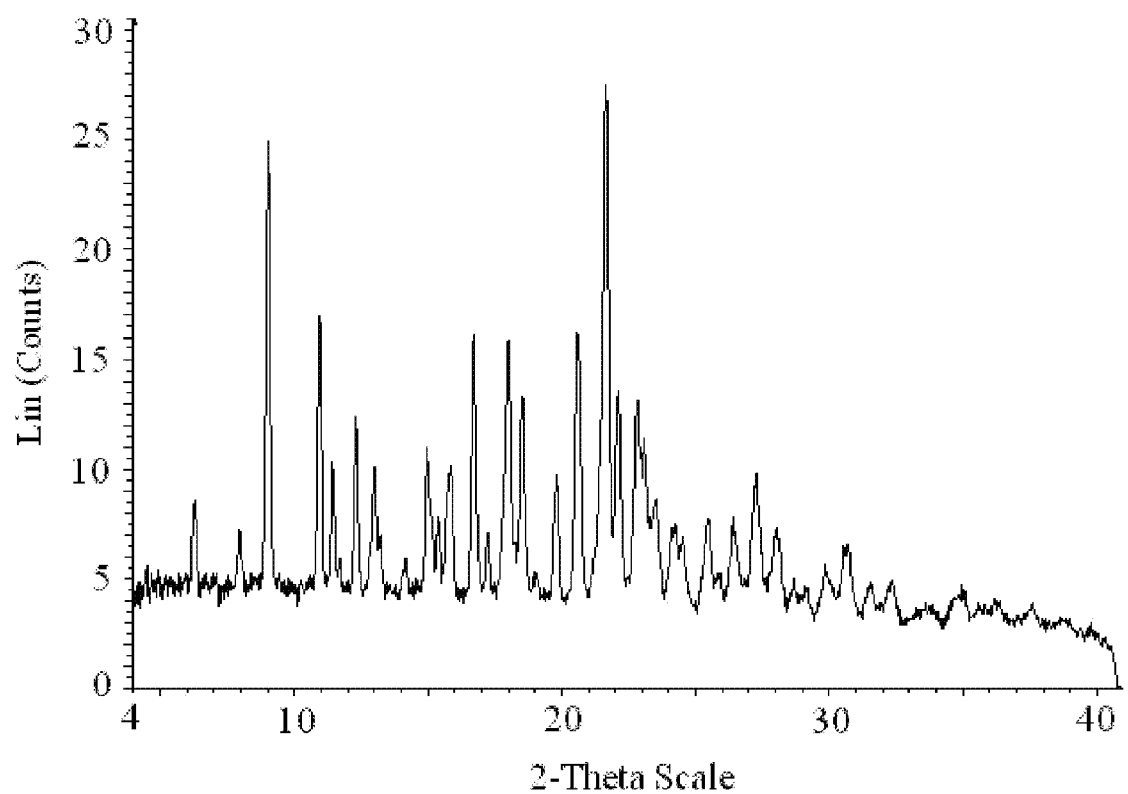
FIG. 6 provides an X-ray diffraction pattern of Compound 1, 2-Propanol Solvate Form A.
Figure 7:
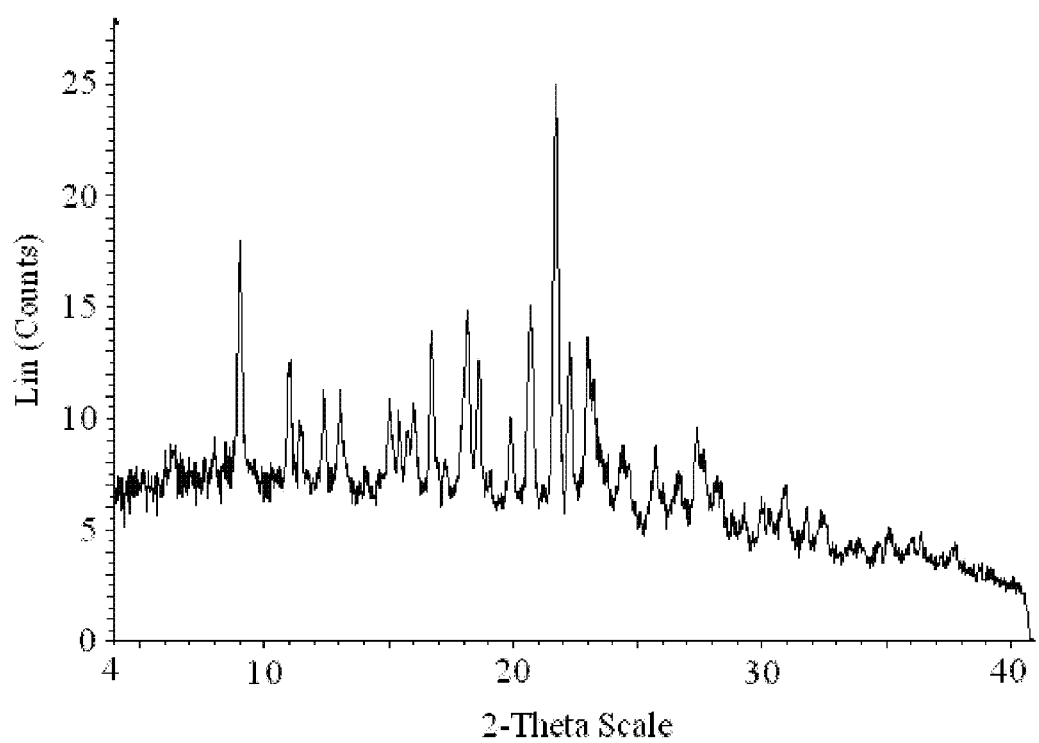
FIG. 7 provides an X-ray diffraction pattern of Compound 1, Acetonitrile Solvate Form A.
Figure 8:
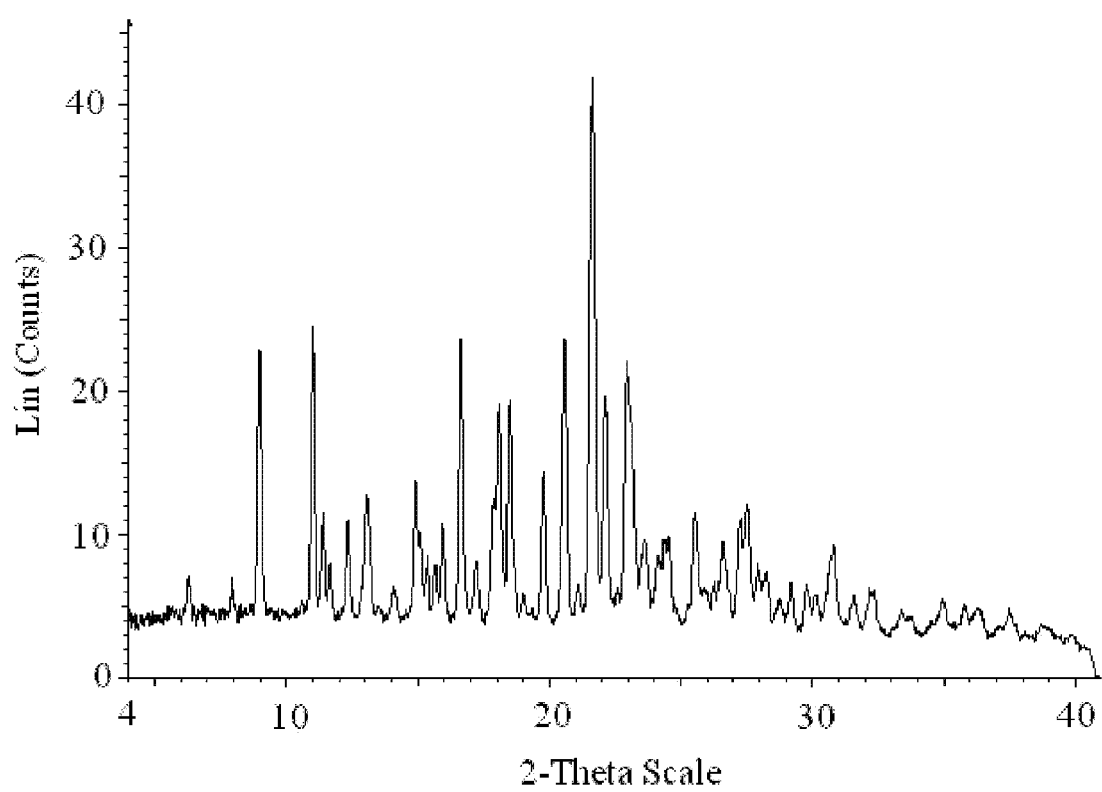
FIG. 8 provides an X-ray diffraction pattern of Compound 1, Tetrahydrofuran Solvate Form A.
Figure 9:
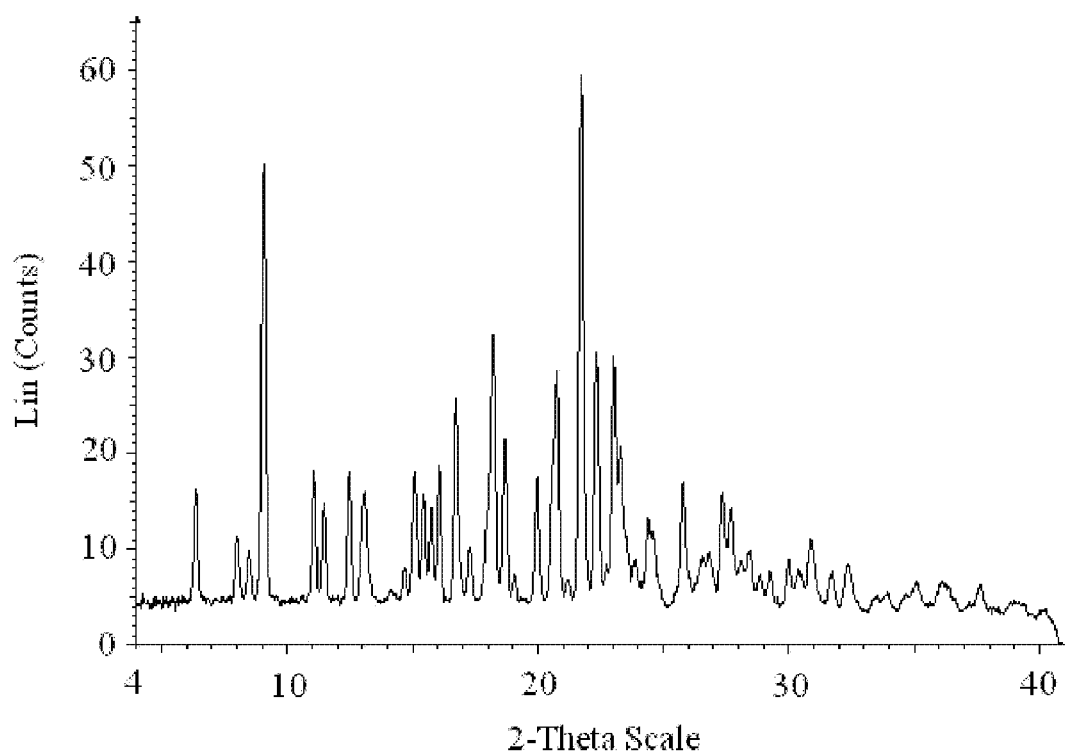
FIG. 9 provides an X-ray diffraction pattern of Compound 1, Methyl Acetate Solvate Form A.
Figure 10:
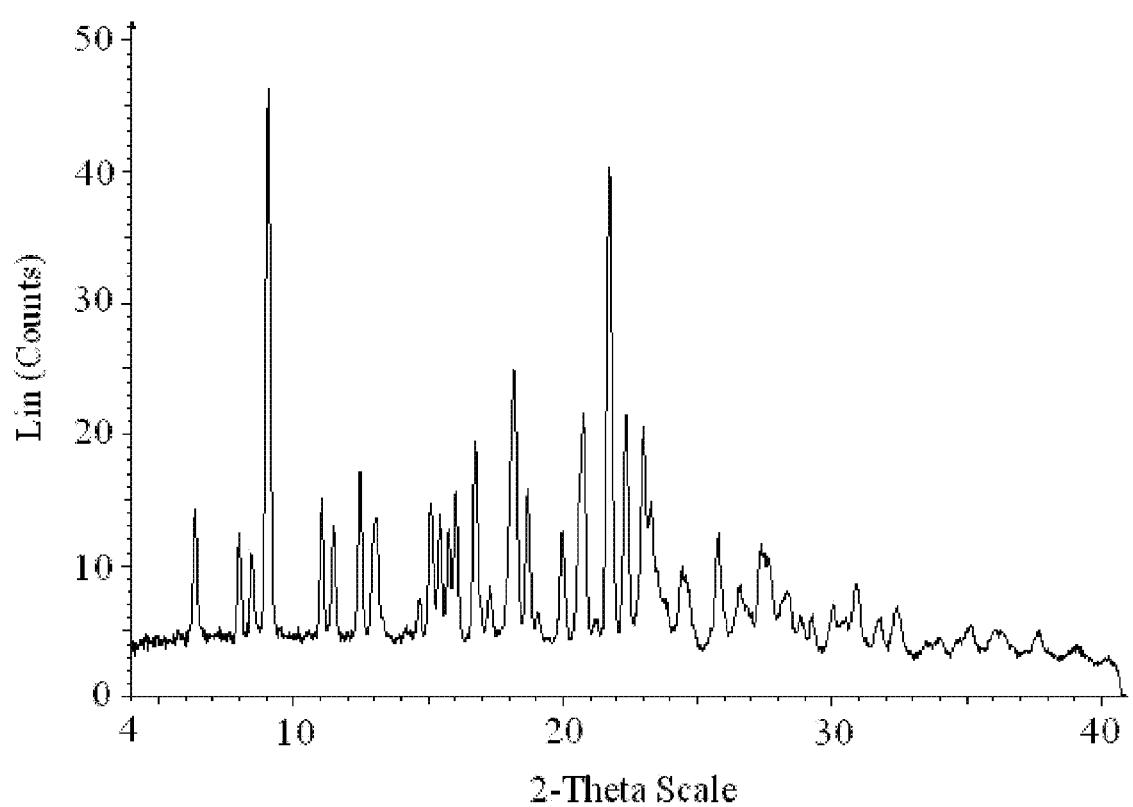
FIG. 10 provides an X-ray diffraction pattern of Compound 1, 2-Butanone Solvate Form A.
Figure 11:
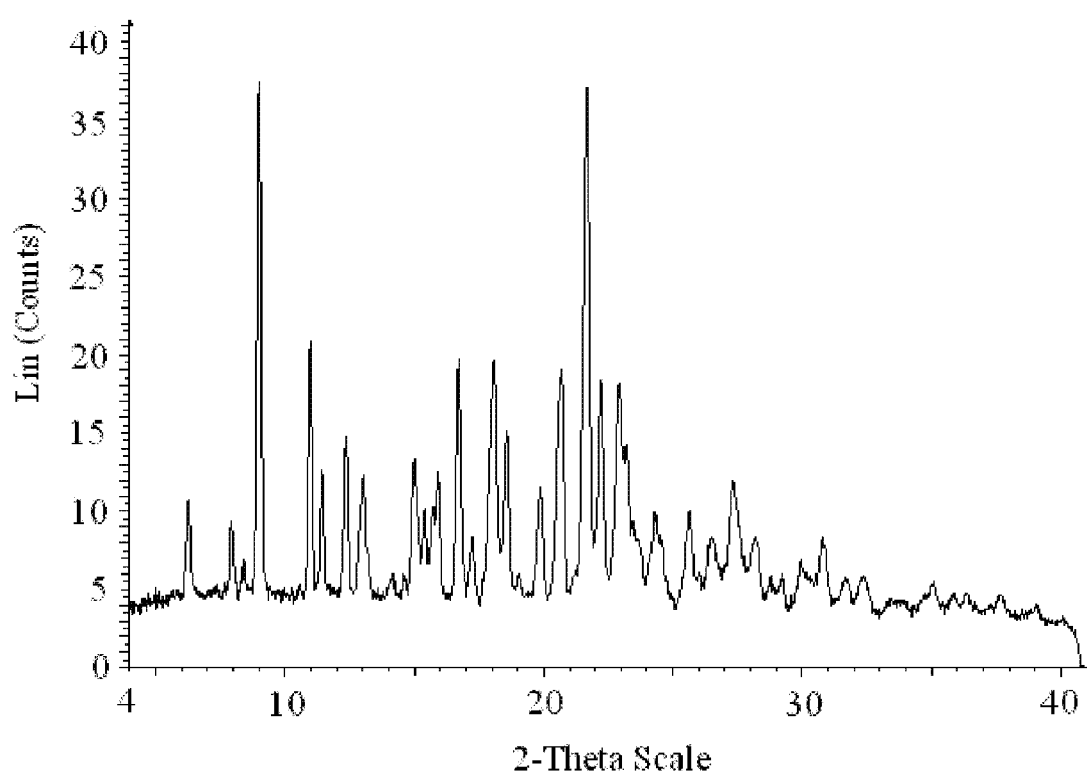
FIG. 11 provides an X-ray diffraction pattern of Compound 1, Ethyl Formate Solvate Form A.
Figure 12:
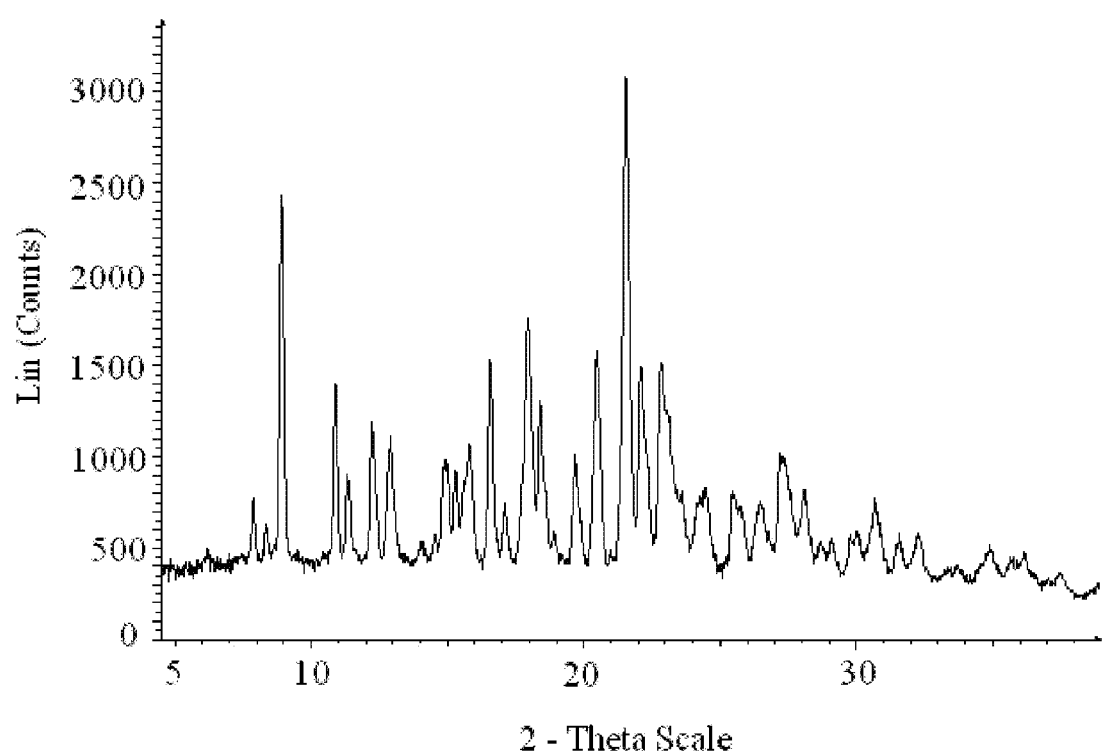
FIG. 12 provides an X-ray diffraction pattern of Compound 1, 2-Methyltetrahydrofuran Solvate Form A.

In another embodiment, the solvate that forms Compound 1, Solvate Form A is selected from the group consisting of methanol, ethanol, acetone, 2-propanol, acetonitrile, tetrahydrofuran, methyl acetate, 2-butanone, ethyl formate, and 2-methyl tetrahydrofuran. Diffraction patterns are provided for the following Compound 1, Solvate A forms: methanol (FIG. 3), ethanol (FIG. 4), acetone (FIG. 5), 2-propanol (FIG. 6), acetonitrile (FIG. 7), tetrahydrofuran (FIG. 8), methyl acetate (FIG. 9), 2-butanone (FIG. 10), ethyl formate (FIG. 11), and 2-methyltetrahydrofuran (FIG. 12).

In another embodiment, the invention features crystalline Compound 1, Acetone Solvate Form A having a P2$_1$/n space group and the following unit cell dimensions: a=16.5235 (10) Å, b=12.7425 (8) Å, c=20.5512 (13) Å, α=90°, β=103.736 (4)°, and γ=90°.

In another embodiment, the invention provides Compound 1, Solvate Form A which exhibits two or more phase transitions as determined by DSC or a similar analytic method known to the skilled artisan. In some embodiments, the DSC of Compound 1, Solvate Form A is substantially similar to the DSC trace depicted in FIG. 13.

In another embodiment of this aspect, the DSC gives two phase transitions.

In another embodiment, the DSC gives three phase transitions.

In another embodiment, one of the phase transitions occurs between 200 and 207° C.

In another embodiment, one of the phase transitions occurs between 204 and 206° C.

In another embodiment, one of the phase transitions occurs between 183 and 190° C.

In another embodiment, one of the phase transitions occurs between 185 and 187° C.

In another embodiment, the melting point of Compound 1, Solvate Form A is between 183° C. to 190° C.

In another embodiment, the melting point of Compound 1, Solvate Form A is between 185° C. to 187° C.

Figure 14:
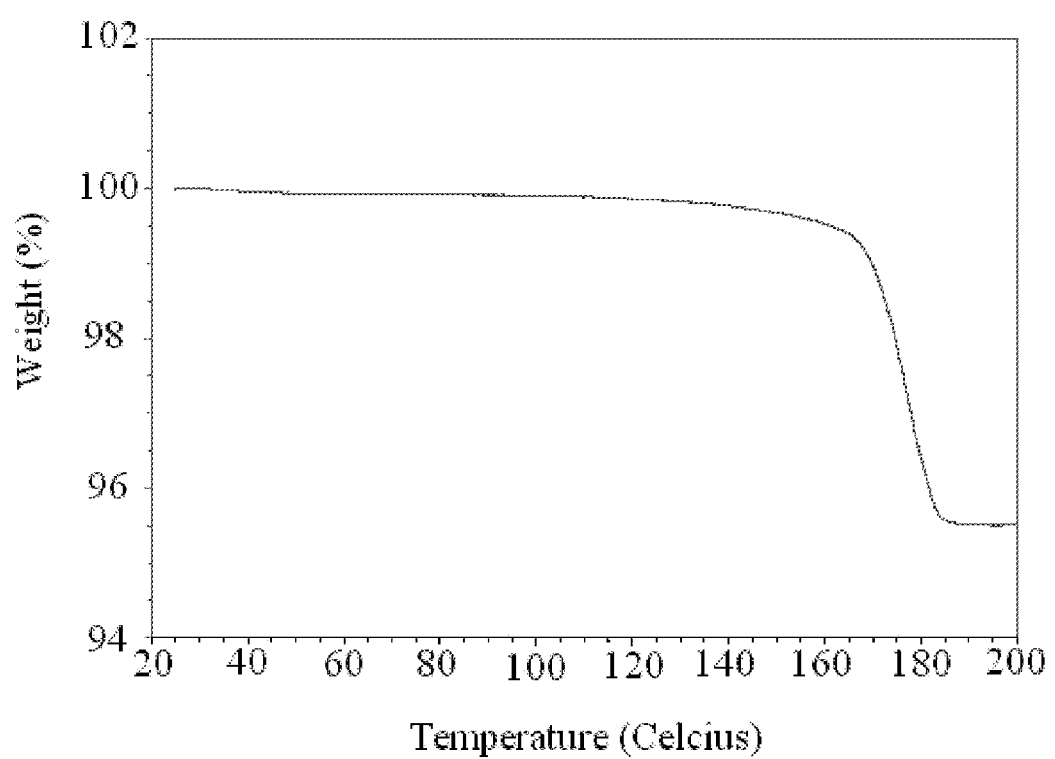
FIG. 14 is a Thermogravimetric analysis (TGA) plot of Compound 1, Acetone Solvate Form A.

In another embodiment, Compound 1, Solvate Form A comprises 1 to 10 weight percent (wt. %) solvate as determined by TGA. In some embodiments, the TGA of Compound 1, Solvate Form A is substantially similar to the TGA trace depicted in FIG. 14.

In another embodiment, Compound 1, Solvate Form A comprises 2 to 5 wt. % solvate as determined by TGA or a similar analytic method known to the skilled artisan.

Figure 15:
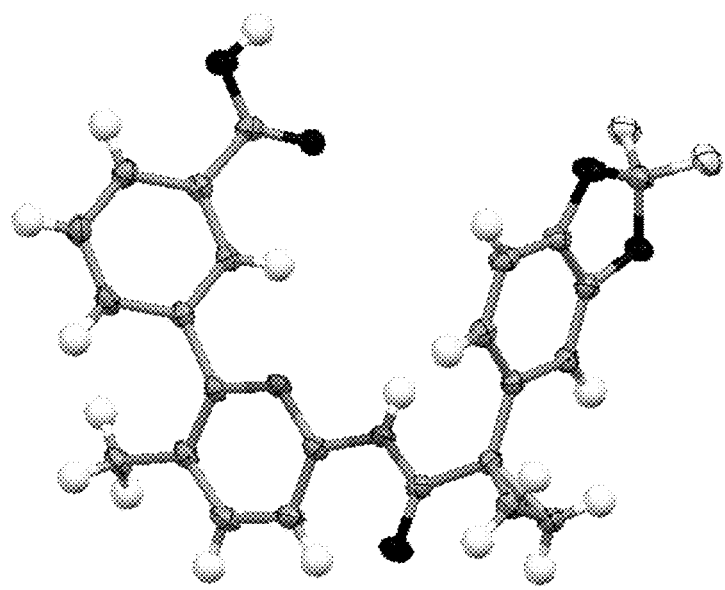
FIG. 15 is a conformational image of Compound 1, Acetone Solvate Form A based on single crystal X-ray analysis.

In another embodiment, the conformation of Compound 1, Acetone Solvate Form A is substantially similar to that depicted in FIG. 15, which is based on single X-ray analysis.

In another embodiment, Compound 1, Acetone Solvate Form A has a P2$_1$/n space group, and the following unit cell dimensions:
a=16.5235 (10) Å α=90°
b=12.7425 (8) Å β=103.736 (4)°
c=20.5512 (13) Å γ=90°.
Compound 1, HCl Salt Form A In another aspect, the invention provides another Compound 1 solid form which is a crystalline HCl salt. This solid form is designated as Compound 1, HCl Salt Form A.

In one embodiment, Compound 1, HCl Salt Form A is characterized by one or more peaks at 8.80 to 9.20 degrees, 17.30 to 17.70 degrees, and 18.20 to 18.60 degrees in an X-ray powder diffraction obtained using Cu K alpha radiation.

In another embodiment, Compound 1, HCl Salt Form A is characterized by one or more peaks at 8.80 to 9.20 degrees, 17.30 to 17.70 degrees, 18.20 to 18.60 degrees, 10.10 to 10.50, and 15.80 to 16.20 degrees in an X-ray powder diffraction obtained using Cu K alpha radiation.

In another embodiment, Compound 1, HCl Salt Form A is characterized by one or more peaks at 8.96, 17.51, and 18.45 degrees.

In another embodiment, Compound 1, HCl Salt Form A is characterized by one or more peaks at 8.96, 17.51, 18.45, 10.33, and 16.01 degrees.

In another embodiment, Compound 1, HCl Salt Form A is characterized by a peak at 8.80 to 9.20 degrees.

In another embodiment, Compound 1, HCl Salt Form A is characterized by a peak at 8.96 degrees.

In another embodiment, Compound 1, HCl Salt Form A is further characterized by a peak at 17.30 to 17.70 degrees.

In another embodiment, Compound 1, HCl Salt Form A is characterized by a peak at 17.51 degrees.

In another embodiment, Compound 1, HCl Salt Form A is further characterized by a peak at 18.20 to 18.60 degrees.

In another embodiment, Compound 1, HCl Salt Form A is further characterized by a peak at 18.45 degrees.

In another embodiment, Compound 1, HCl Salt Form A is further characterized by a peak at 10.10 to 10.50 degrees.

In another embodiment, Compound 1, HCl Salt Form A is further characterized by a peak at 10.33 degrees.

In another embodiment, Compound 1, HCl Salt Form A is further characterized by a peak at 15.80 to 16.20 degrees.

In another embodiment, Compound 1, HCl Salt Form A is further characterized by a peak at 16.01 degrees.

In another embodiment, Compound 1, HCl Salt Form A is further characterized by a peak at 11.70 to 12.10 degrees.

In another embodiment, Compound 1, HCl Salt Form A is further characterized by a peak at 11.94 degrees.

In another embodiment, Compound 1, HCl Salt Form A is further characterized by a peak at 7.90 to 8.30 degrees.

In another embodiment, Compound 1, HCl Salt Form A is further characterized by a peak at 8.14 degrees.

In another embodiment, Compound 1, HCl Salt Form A is further characterized by a peak at 9.90 to 10.30 degrees.

In another embodiment, Compound 1, HCl Salt Form A is further characterized by a peak at 10.10 degrees.

In another embodiment, Compound 1, HCl Salt Form A is further characterized by a peak at 16.40 to 16.80 degrees.

In another embodiment, Compound 1, HCl Salt Form A is further characterized by a peak at 16.55 degrees.

In another embodiment, Compound 1, HCl Salt Form A is further characterized by a peak at 9.30 to 9.70 degrees.

In another embodiment, Compound 1, HCl Salt Form A is further characterized by a peak at 9.54 degrees.

In another embodiment, Compound 1, HCl Salt Form A is further characterized by a peak at 16.40 to 16.80 degrees.

In another embodiment, Compound 1, HCl Salt Form A is further characterized by a peak at 16.55 degrees.

Figure 19:
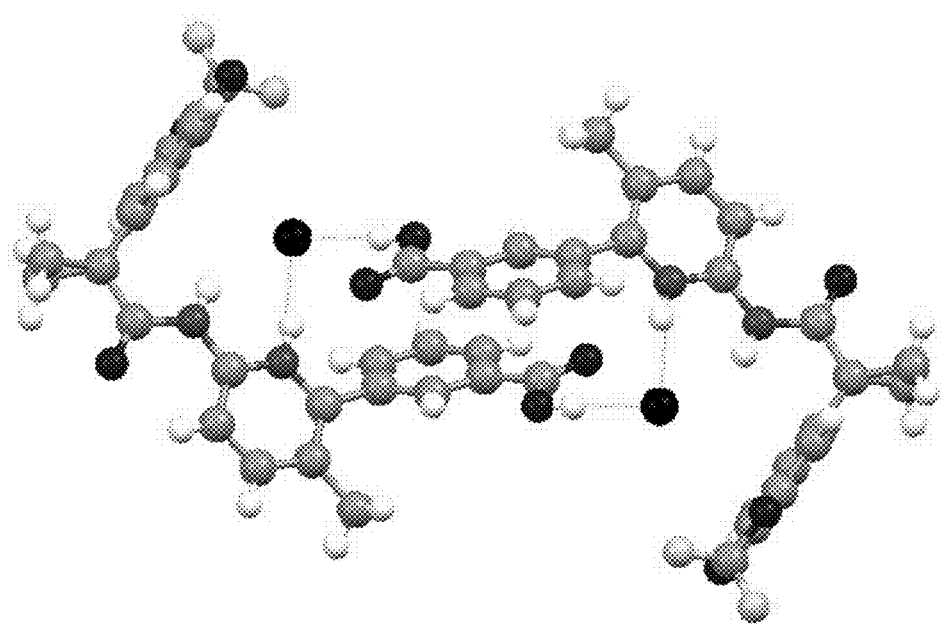
FIG. 19 is a conformational image of the dimer of Compound 1, HCl Salt Form A.

In some embodiments, Compound 1, HCl Salt Form A is characterized as a dimer, as depicted in FIG. 19.

Figure 20:
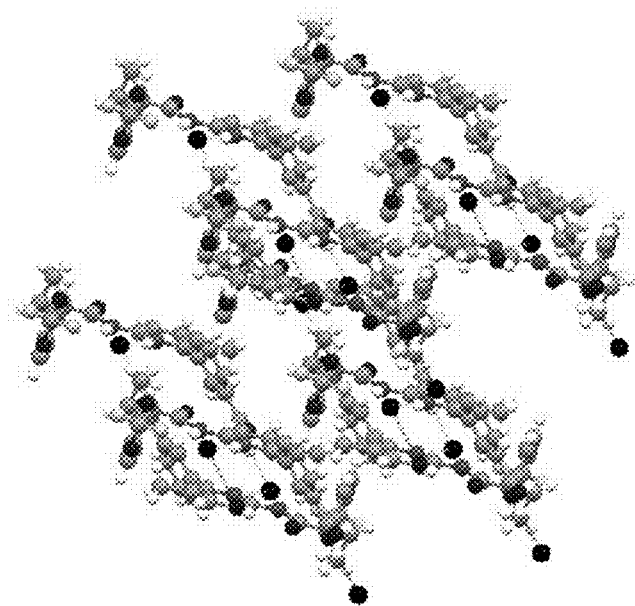
FIG. 20 is a packing diagram of Compound 1, HCl Salt Form A.

In some embodiments, Compound 1, HCl Salt Form A is characterized by the packing diagram depicted in FIG. 20.

Figure 21:
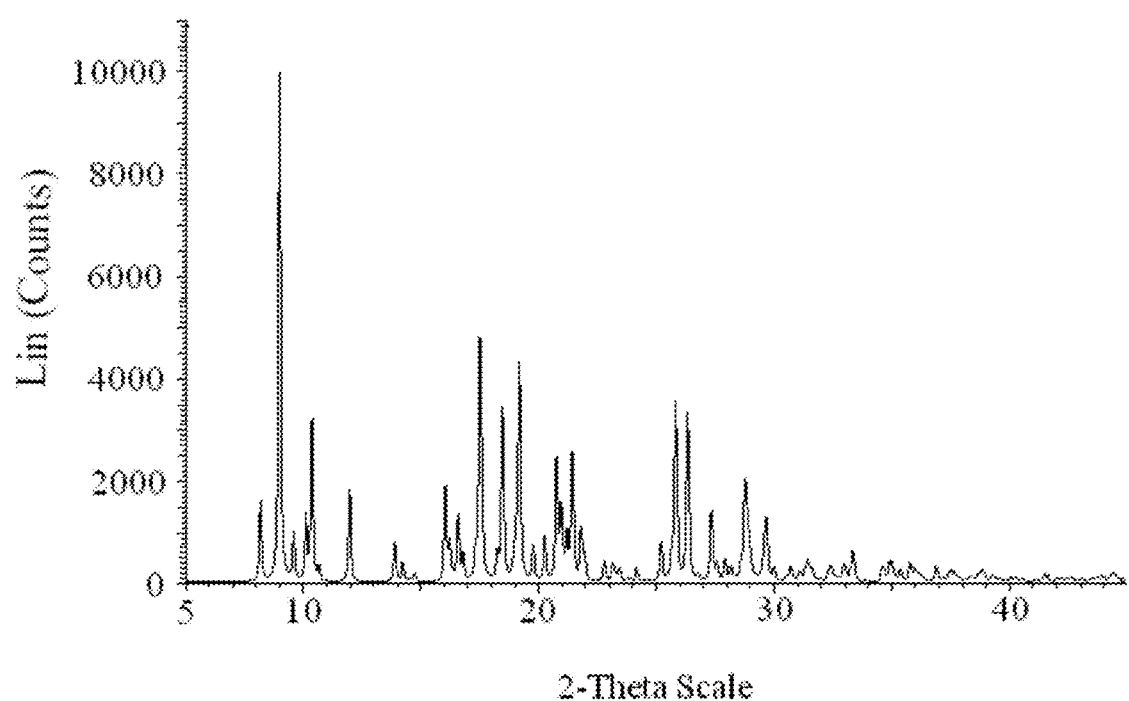
FIG. 21 is an X-ray diffraction pattern of Compound 1, HCl Salt Form A calculated from the crystal structure.

In some embodiments, Compound 1, HCl Salt Form A is characterized by a diffraction pattern substantially similar to that of FIG. 21.

In another embodiment, the invention features crystalline Compound 1, HCl Salt Form A having a P$^-$1 space group and the following unit cell dimensions: a=10.2702 (2) Å, b=10.8782 (2) Å, c=12.4821 (3) Å, α=67.0270 (10)°, β=66.1810 (10)°, and γ=72.4760 (10)°.

In another embodiment, the invention features a kit comprising Compound 1, Solvate Form A or Compound 1, HCl Salt Form A and instructions for use thereof.
Synthesis of Compound 1, Solvate Form A and Compound 1, HCl Salt Form A The solid forms of the invention designated and described above as Compound 1, Solvate Form A and Compound 1, HCl Salt Form A, can be prepared from precursors including Compound 1 and from other solid forms of Compound 1. This section describes the synthesis of Compound 1 and other solid forms of Compound 1, as well as the conversion of these other solid forms to the solid forms of the invention designated as Compound 1, Solvate Form A and Compound 1, HCl Salt Form A.

corresponding primary alkyl chloride 5-(chloromethyl)-2,2-difluorobenzo[d][1,3]dioxole using thionyl chloride. The alkyl chloride is subsequently converted to the nitrile 2-(2,2-

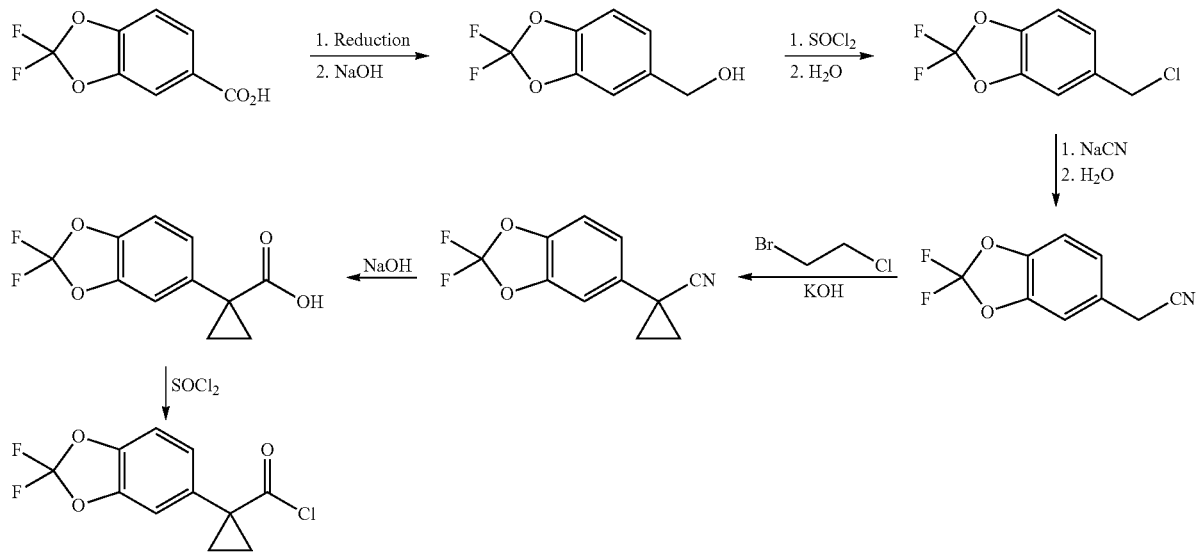

Scheme 1. Synthesis of the acid chloride used to prepare Compound 1.

Scheme 1 depicts the preparation of 1-(2,2-difluorobenzo[d][1,3]dioxol-5-yl)cyclopropanecarbonyl chloride, which is used to make Compound 1 (See Scheme 4). The starting material, 2,2-difluorobenzo[d][1,3]dioxole-5-carboxylic acid, is commercially available from Saltigo (an affiliate of the Lanxess Corporation). Reduction of the carboxylic acid moiety in 2,2-difluorobenzo[d][1,3]dioxole-5-carboxylic acid provides the primary alcohol, which is converted to the difluorobenzo[d][1,3]dioxol-5-yl)acetonitrile by displacement using sodium cyanide. Treatment of the nitrile with 1-bromo-2-chloroethane in the presence of base provides 1-(2,2-difluorobenzo[d][1,3]dioxol-5-yl)cyclopropanecarbonitrile. Conversion of the nitrile to 1-(2,2-difluorobenzo[d][1,3]dioxol-5-yl)cyclopropanecarboxylic acid under basic conditions, followed by treatment with thionyl chloride, provides the requisite acid chloride.

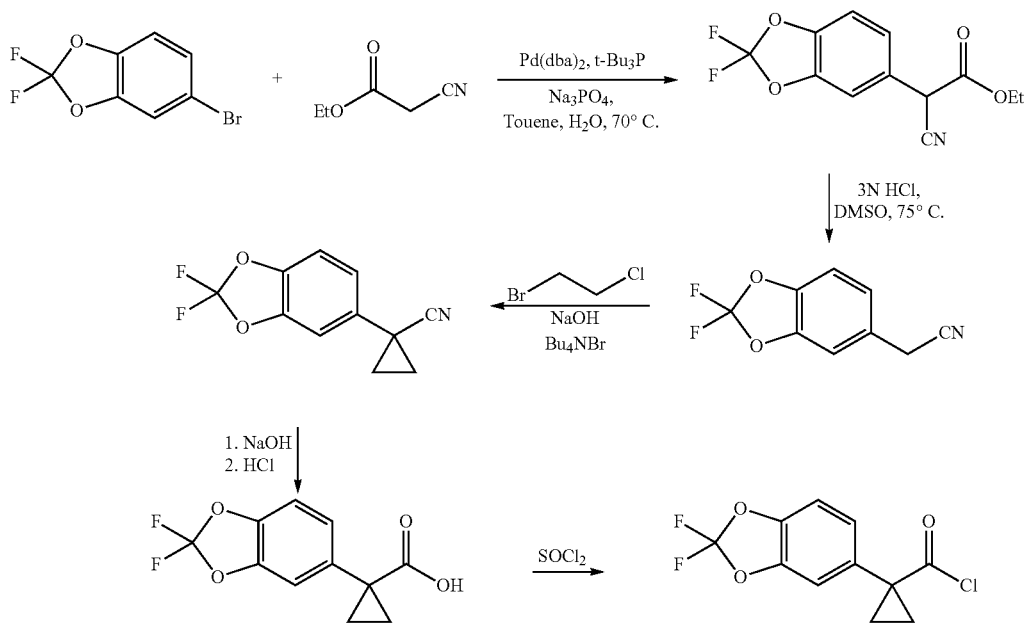

Scheme 2. Alternative synthesis of the requisite acid chloride.

Scheme 2 provides an alternative synthesis of the requisite acid chloride. The compound 5-bromomethyl-2,2-difluoro-1,3-benzodioxole is coupled with ethyl cyanoacetate in the presence of a palladium catalyst to form the corresponding alpha cyano ethyl ester. Saponification of the ester moiety to the carboxylic acid gives the cyanoethyl compound. Alkylation of the cyanoethyl compound with 1-bromo-2-chloro ethane in the presence of base gives the cyanocyclopropyl compound. Treatment of the cyanocyclopropyl compound with base gives the carboxylate salt, which is converted to the carboxylic acid by treatment with acid. Conversion of the carboxylic acid to the acid chloride is then accomplished using a chlorinating agent such as thionyl chloride or the like.

Scheme 3. Synthesis of the amine used to prepare Compound 1.

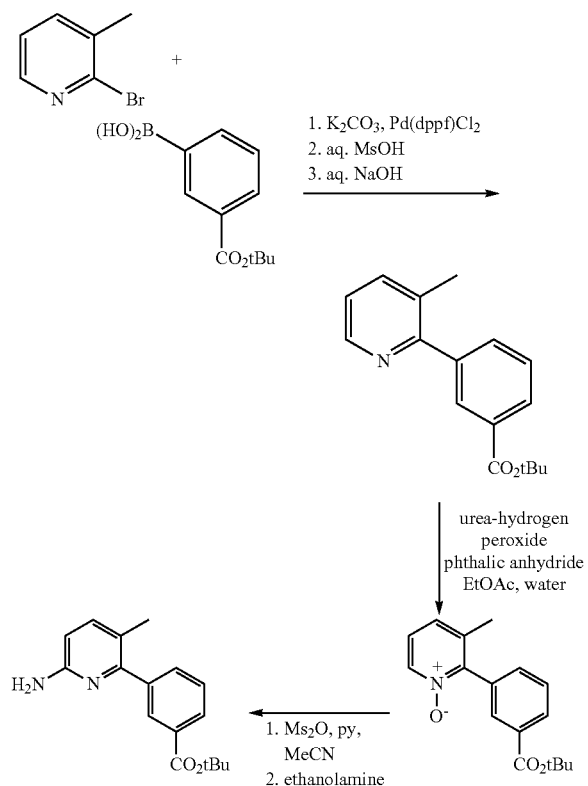

Scheme 3 depicts the preparation of tert-butyl 3-(6-amino-3-methylpyridin-2-yl)benzoate, which is coupled with 1-(2,2-difluorobenzo[d][1,3]dioxol-5-yl)cyclopropanecarbonyl chloride (See Schemes 1 and 2) in Scheme 4 to give Compound 1 as an acid salt. Palladium-catalyzed coupling of 2-bromo-3-methylpyridine with 3-(tert-butoxycarbonyl)phenylboronic acid gives tert-butyl 3-(3-methylpyridin-2-yl)benzoate, which is subsequently converted via a series of steps to the desired compound.

Scheme 4. Formation of an acid salt of Compound 1.

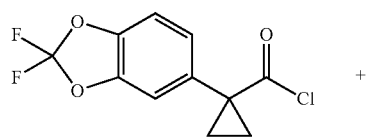

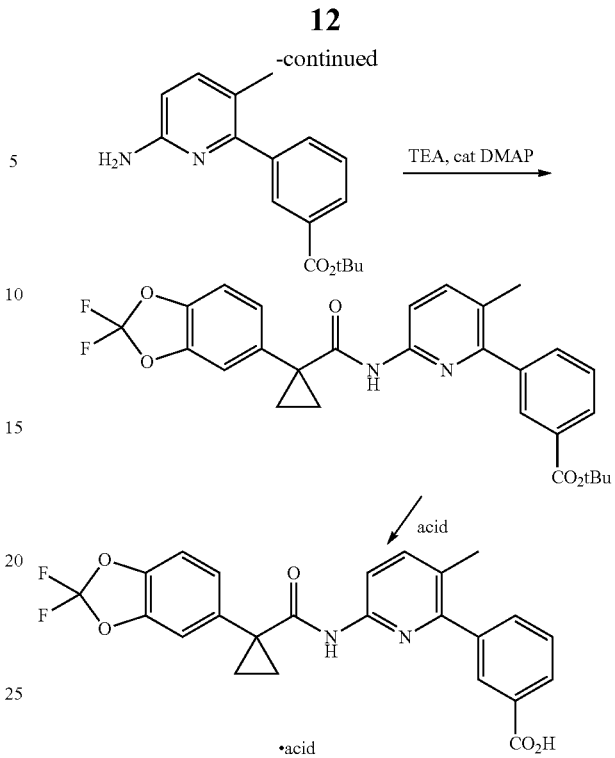

Compound 1 is prepared as an acid salt as provided in Scheme 4. Coupling the acid chloride of Schemes 1 or 2 with the amine of Scheme 3 using triethyl amine and catalytic 4-dimethylaminopyridine or the like initially provides the tert-butyl ester 3-(6-(1-(2,2-difluorobenzo[d][1,3]dioxol-5-yl)cyclopropanecarboxamido)-3-methylpyridin-2-yl)-t-butylbenzoate, which is the tert-butyl ester precursor of Compound 1. Treatment of the tert-butyl ester with an acid, such as HCl, gives the HCl salt of Compound 1. The HCl salt of Compound 1, which is typically a crystalline solid, can be used to prepare other solid forms of Compound 1, including the solid forms of the invention, Compound 1, Solvate From A and Compound 1, HCl Salt Form A.

Preparation of Compound 1, Solvate Form A from the HCl Salt of Compound 1

Compound 1, Solvate Form A can be prepared by dispersing or dissolving a salt form, such as the HCl salt of Compound 1, in an appropriate solvent for an effective amount of time, followed by isolation of crystalline Compound 1, Solvate Form A by filtration.

Preparation of Compound 1, HCl Salt Form A from the HCl Salt of Compound 1

Compound 1, HCl Salt Form A can be prepared from the HCl salt of Compound 1 by dissolving the HCl salt of Compound 1 in a minimum of solvent and removing the solvent by slow evaporation. In an embodiment, the solvent is an alcohol. In another embodiment, the solvent is ethanol. Slow evaporation is generally carried out by impeding the evaporation of the solvent. For example, in one embodiment, slow evaporation involves dissolving the HCl salt of Compound 1 in a vial and covering the vial with parafilm that contains a hole poked in it.

Preparation of Compound 1, Solvate Form A from Compound 1, Form I

Compound 1, Form 1 (described above and as disclosed in U.S. patent application Ser. No. 12/327,902, filed Dec. 4, 2008) is another solid form of Compound 1 that can be used to prepare the solid forms of the invention, particularly Compound 1, Solvate Form A.

Compound 1, Form 1 can be prepared from the HCl salt of Compound 1 by dispersing or dissolving the HCl salt in an appropriate solvent for an effective amount of time. The appropriate solvent may be water or an alcohol/water mixture, such as a 50% methanol/water mixture, even though the HCl salt form of Compound 1 is only sparingly soluble in water. Alternatively, the appropriate solvent is water.

Other acid salts of Compound 1 may also be used to prepare Compound 1, Form 1, such as, for example, salts derived from other mineral or organic acids. The other salts also result from acid-mediated hydrolysis of the tert-butyl ester precursor of Compound 1 (See Scheme 4). Salts derived from other acids may include, for example, nitric, sulfuric, phosphoric, boric, acetic, benzoic, and malonic. These salt forms of Compound 1 may or may not be soluble, depending upon the solvent used, but lack of solubility does not hinder formation of Compound 1, Form I. The effective amount of time for formation of Compound 1, Form I from a salt of Compound 1 can be any time between 2 and 24 hours or greater. It is recognized that the amount of time needed is inversely proportional to the temperature. That is, the higher the temperature, the less time needed to affect dissociation of acid to form Compound 1, Form I. When the solvent is water, stifling the dispersion for approximately 24 hours at room temperature provides Form I in an approximately 98% yield. If a solution of the salt of Compound 1 is desired for process purposes, an elevated temperature may be used. After stirring the solution for an effective amount of time at the elevated temperature, recrystallization upon cooling provides substantially pure Compound 1, Form I. "Substantially pure" refers to greater than about 90% purity, or greater than about 95% purity, or greater than about 98% purity, or greater than about 99% purity. The temperature selected depends in part on the solvent used and is well within the determination capabilities of one of ordinary skill in the art and is typically between room temperature and about 80° C.

Alternatively, Compound 1, Form I can be formed directly from the tert-butyl ester precursor of Compound 1 (See Scheme 4) by treatment with an appropriate acid, such as, for example, formic acid, under appropriate reaction conditions to give Compound 1, Form I. For example, the tert-butyl ester is reacted with an appropriate acid, such as formic acid, at 60 to 80° C. for 7 to 9 hours before cooling to ambient temperatures, adding the reaction mixture to water, and reheating to 60 to 80° C. for an effective amount of time. Compound 1, Form 1 is then isolated by filtration.

Compound 1, Form I may be further purified by recrystallization from an organic solvent. Examples of organic solvents include, but are not limited to, toluene, cumene, anisol, 1-butanol, isopropyl acetate, butyl acetate, isobutyl acetate, methyl t-butyl ether, methyl isobutyl ketone, and 1-propanol-water mixtures. The temperature may be as described above. For example, Compound 1, Form I is dissolved in 1-butanol at 75° C. until it is completely dissolved. Cooling down the solution to 10° C. at a rate of 0.2° C./min yields crystals of Compound 1, Form I which may be isolated by filtration.

As indicated, Compound 1, Form 1 can be used to prepare Compound 1, Solvate Form A. Accordingly, an amount of Compound 1, Form I is slurried in an appropriate solvent at a sufficient concentration for a sufficient time. The slurry is then filtered centrifugally or under vacuum and dried at ambient conditions for sufficient time to yield Compound 1, Solvate Form A.

In some embodiments, about 20 to 40 mg of Compound 1, Form I is slurried in about 400 to 600 µL of an appropriate solvent. In another embodiment, about 25 to 35 mg of Compound 1, Form I is slurried in about 450 to 550 µL of an appropriate solvent. In another embodiment, about 30 mg of Compound 1, Form I is slurried in about 500 µL of an appropriate solvent.

In some embodiments, the time that Compound 1, Form I is allowed to slurry with the solvent is between 1 hour and four days. More particularly, the time that Compound 1, Form I is allowed to slurry with the solvent is between 1 and 3 days. More particularly, the time is 2 days.

In some embodiments, the appropriate solvent is selected from an organic solvent of sufficient size to fit the voids in the crystalline lattice of Compound 1. In other embodiments, the solvate is of sufficient size to fit in voids measuring about 100 $Å^3$.

In other embodiments, the solvent is selected from the group consisting of methanol, ethanol, acetone, 2-propanol, acetonitrile, tetrahydrofuran, methyl acetate, 2-butanone, ethyl formate, and 2-methyl tetrahydrofuran.

In other embodiments, a mixture of two or more of these solvents may be used to obtain Compound 1, Solvate Form A. Alternatively, Compound 1, Solvate Form A may be obtained from a mixture comprising one or more of these solvents and water.

In some embodiments, the effective amount of time for drying Compound 1, Solvate Form A is 1 to 24 hours. More particularly, the time is 6 to 18 hours. More particularly, the time is about 12 hours.

Uses, Compositions and Administration
Pharmaceutically Acceptable Compositions

In another aspect of the present invention, pharmaceutically acceptable compositions are provided, wherein these compositions comprise Compound 1, Solvate Form A or Compound 1, HCl Salt Form A, as described herein, and optionally comprise a pharmaceutically acceptable carrier, adjuvant, or vehicle. In certain embodiments, these compositions optionally further comprise one or more additional therapeutic agents.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers; alumina; aluminum stearate; lecithin; serum proteins, such as human serum albumin; buffer substances, such as phosphates, glycine, sorbic acid, or potassium sorbate; partial glyceride mixtures of saturated vegetable fatty acids; water; salts, or electrolytes, such as protamine sulfate, disodium hydrogen phosphate, potassium hydrogen phosphate, sodium chloride, zinc salts, colloidal silica, or magnesium trisilicate; polyvinyl pyrrolidone; polyacrylates; waxes; polyethylene-polyoxypropylene-block polymers; wool fat; sugars, such as lactose, glucose, or sucrose; starches, such as corn starch and potato starch; cellulose and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, or soybean oil; glycols, such as propylene glycol or polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; and phosphate buffer solutions, as well as other non-toxic compatible lubricants, such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Methods of Treatment

In yet another aspect, the present invention provides a method of treating a condition, disease, or disorder implicated by CFTR. In certain embodiments, the present invention provides a method of treating a condition, disease, or disorder implicated by a deficiency of CFTR activity, the method comprising administering a composition comprising a solid state form of Compound 1 selected from Compound 1, Solvate Form A and Compound 1, HCl Salt Form A, described herein, to a subject, preferably a mammal, in need thereof.

As used herein, a "CFTR-mediated disease" is a disease selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, protein C deficiency, Type 1 hereditary angioedema, lipid processing deficiencies, familial hypercholesterolemia, Type 1 chylomicronemia, abetalipoproteinemia, lysosomal storage diseases, I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases, Alzheimer's disease, Parkinson's disease, amyotrophic lateral sclerosis, progressive supranuclear plasy, Pick's disease, several polyglutamine neurological disorders, Huntington's, spinocerebullar ataxia type I, spinal and bulbar muscular atrophy, dentatorubal pallidoluysian, myotonic dystrophy, spongiform encephalopathies, hereditary Creutzfeldt-Jakob disease (due to prion protein processing defect), Fabry disease, Straussler-Scheinker syndrome, COPD, dry-eye disease, Sjogren's disease, Osteoporosis, Osteopenia, Gorham's Syndrome, chloride channelopathies, myotonia congenita (Thomson and Becker forms), Bartter's syndrome type III, Dent's disease, hyperekplexia, epilepsy, hyperekplexia, lysosomal storage disease, Angelman syndrome, Primary Ciliary Dyskinesia (PCD), inherited disorders of the structure and/or function of cilia, PCD with situs inversus (also known as Kartagener syndrome), PCD without situs inversus, or ciliary aplasia.

In certain embodiments, the present invention provides a method of treating a CFTR-mediated disease in a human comprising the step of administering to said human an effective amount of a composition comprising Compound 1, Solvate Form A or Compound 1, HCl Salt Form A, described herein.

According to an alternative preferred embodiment, the present invention provides a method of treating cystic fibrosis in a human comprising the step of administering to said human a composition comprising Compound 1, Solvate Form A or Compound 1, HCl Salt Form A described herein.

In another embodiment, said human has cystic fibrosis transmembrane receptor (CFTR) with a ΔF508 mutation. In another embodiment, said human has cystic fibrosis transmembrane receptor (CFTR) with a R117H mutation. In another embodiment, said human has cystic fibrosis transmembrane receptor (CFTR) with a G551D mutation.

According to the invention, an "effective amount" of Compound 1, Solvate Form A or a pharmaceutically acceptable composition thereof is that amount effective for treating or lessening the severity of any of the diseases recited above.

Compound 1, Solvate Form A or Compound 1, HCl Salt Form A, or pharmaceutically acceptable compositions thereof, may be administered using any amount and any route of administration effective for treating or lessening the severity of one or more of the diseases recited above.

In certain embodiments, Compound 1, Solvate Form A or Compound 1, HCl Salt Form A, as described herein, or pharmaceutically acceptable compositions thereof, are useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508.

In one embodiment, Compound 1, Solvate Form A or Compound 1, HCl Salt Form A, as described herein, or pharmaceutically acceptable compositions thereof, are useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Transmembrane Conductance Regulator Defects and Opportunities of Therapy*; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, Compound 1, Solvate Form A or Compound 1, HCl Salt Form A, as described herein, or pharmaceutically acceptable compositions thereof, are useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic insufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form," as used herein, refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors, including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient," or "subject," as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg, and preferably from about 1 mg/kg to about 25 mg/kg, of subject body weight per day, one or more times a day, to obtain the desired therapeutic effect.

In certain embodiments, the dosage amount of Compound 1, Solvate Form A or Compound 1, HCl Salt Form A are in the dosage unit is from 100 mg to 1,000 mg. In another embodiment, the dosage amount of Compound 1, Solvate Form A is from 200 mg to 900 mg. In another embodiment, the dosage amount of Compound 1, Solvate Form A or Compound 1, HCl Salt Form A is from 300 mg to 800 mg. In another embodiment, the dosage amount of Compound 1, Solvate Form A or Compound 1, HCl Salt Form A is from 400 mg to 700 mg. In another embodiment, the dosage amount of Compound 1, Solvate Form A or Compound 1, HCl Salt Form A is from 500 mg to 600 mg.

In another embodiment, the present invention comprises jet milling Compound 1, Solvate Form A or Compound 1, HCl Salt Form A in a suitable, conventional milling apparatus using air pressure suitable to produce particles having a significant particle size fraction between 0.1 microns and 50 microns. In another embodiment, the particle size is between 0.1 microns and 20 microns. In another embodiment, the particles size is between 0.1 microns and 10 microns. In another embodiment, the particle size is between 1.0 microns and 5 microns. In still another embodiment, Compound 1, Solvate Form A or Compound 1, HCl Salt Form A has a particle size D50 of 2.0 microns.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed, including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions, which can be dissolved or dispersed in sterile water or other sterile injectable medium prior to use.

Compositions for rectal or vaginal administration are preferably suppositories which can be prepared by mixing Compound 1, Solvate Form A or Compound 1, HCL Salt Form A with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the Compound 1, Solvate Form A or Compound 1, HCL Salt Form A is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms, the active compound may be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

It will also be appreciated that Compound 1, Solvate Form A or Compound 1, HCl Salt Form A as described herein or pharmaceutically acceptable compositions thereof can be employed in combination therapies, that is, Compound 1, Solvate Form A or Compound 1, HCl Salt Form A can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

In one embodiment, the additional agent is selected from a mucolytic agent, bronchodialator, an anti-biotic, an anti-infective agent, an anti-inflammatory agent, a CFTR modulator other than a compound of the present invention, or a nutritional agent.

In one embodiment, the additional agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide. In another embodiment, the additional agent is N-(5-hydroxy-2,4-ditert-butyl-phenyl)-4-oxo-1H-quinoline-3-carboxamide. In another embodiment, the additional agent is selected from Table 1:

TABLE 1

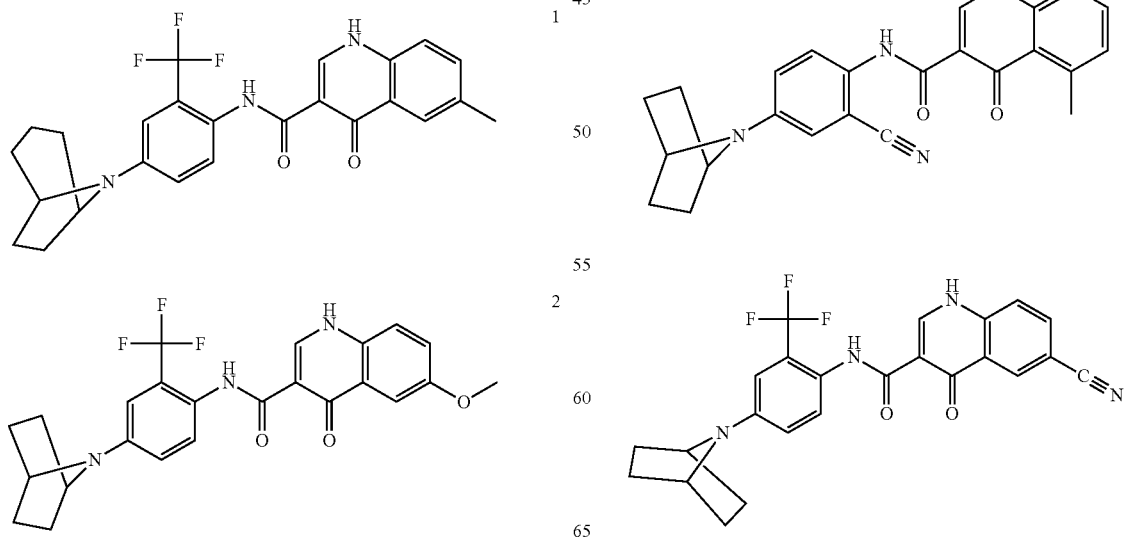

TABLE 1-continued

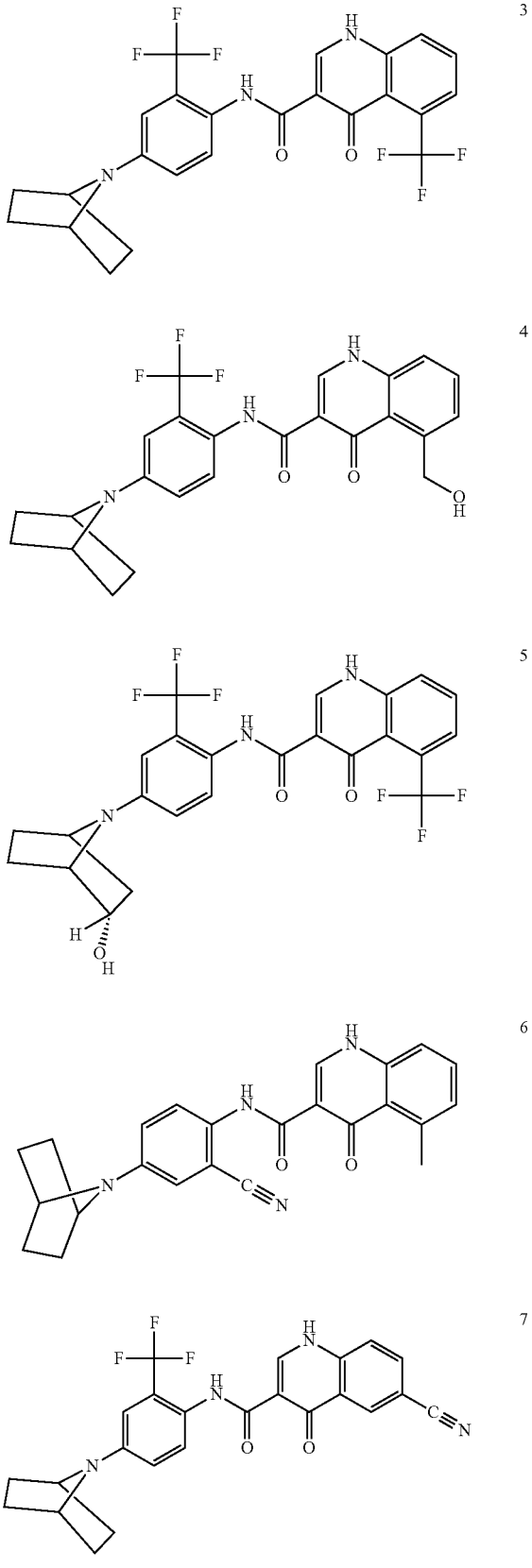

TABLE 1-continued

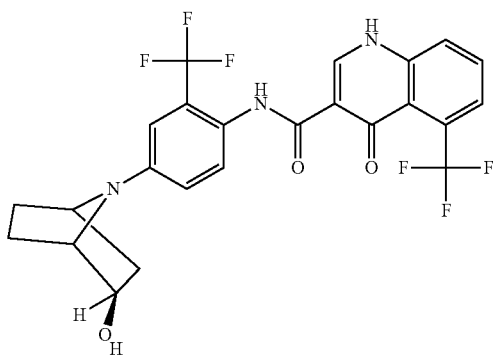
8

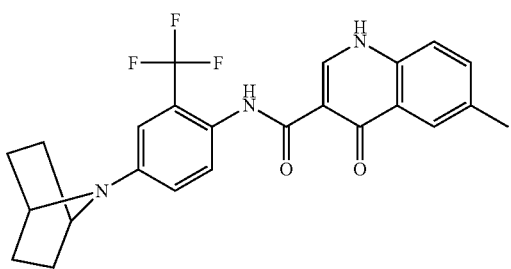 [SMILES: Cc1ccc2[nH]cc(C(=O)Nc3ccc(N4C5CCC4CC5)cc3C(F)(F)F)c(=O)c2c1]
9

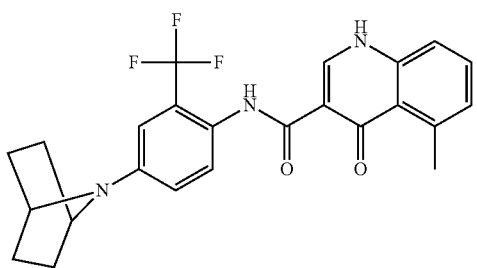 [SMILES: Cc1cccc2[nH]cc(C(=O)Nc3ccc(N4C5CCC4CC5)cc3C(F)(F)F)c(=O)c12]
10

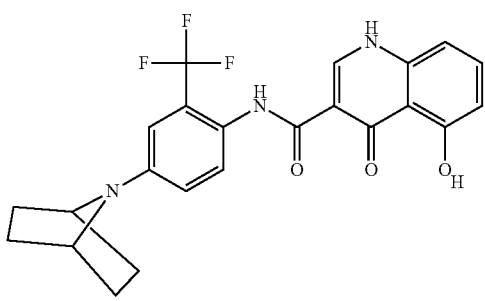
11

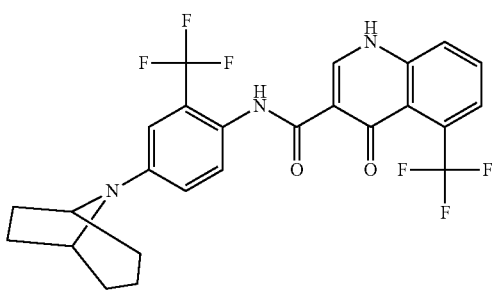 [SMILES: O=C(Nc1ccc(N2C3CCCC2CC3)cc1C(F)(F)F)c1c[nH]c2cccc(C(F)(F)F)c2c1=O]
12

TABLE 1-continued

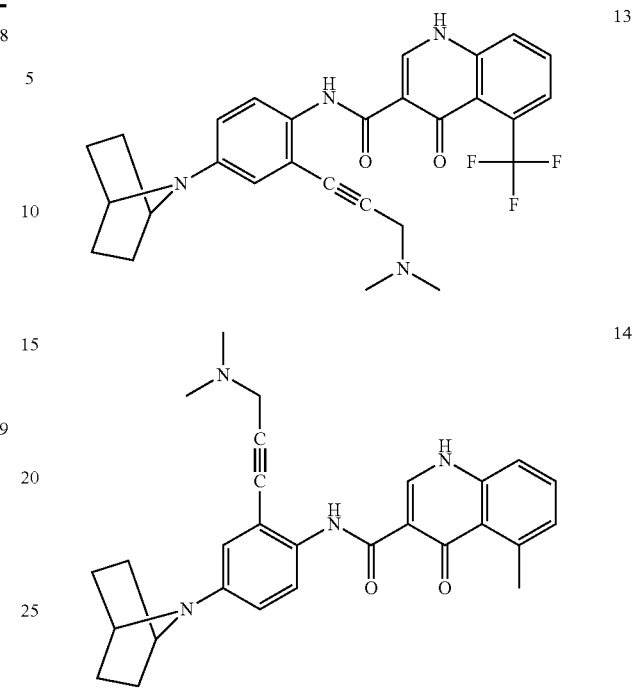
13

14

In another embodiment, the additional agent is any combination of the above agents. For example, the composition may comprise Compound 1, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, and N-(5-hydroxy-2,4-ditert-butyl-phenyl)-4-oxo-1H-quinoline-3-carboxamide. In another example, the composition may comprise Compound 1, N-(5-hydroxy-2,4-ditert-butyl-phenyl)-4-oxo-1H-quinoline-3-carboxamide, and any one of the compounds from Table 1, i.e. compounds 1 through 14 of Table 1, or any combination thereof.

In one embodiment, the additional therapeutic agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional agent is a mucolyte. Exemplary mucolytes useful herein includes Pulmozyme®.

In another embodiment, the additional agent is a bronchodialator. Exemplary bronchodilators include albuterol, metaprotenerol sulfate, pirbuterol acetate, salmeterol, or tetrabuline sulfate.

In another embodiment, the additional agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[[(3S,5R)-5-(4-amino-2-oxopyrimidin-1-yl)-3-hydroxyoxolan-2-yl]methoxy-hydroxyphosphoryl][[[(2R,3S,4R,5R)-5-(2,4-dioxopyrimidin-1-yl)-3,4-dihydroxyoxolan-2-yl]methoxy-hydroxyphosphoryl]oxy-hydroxyphosphoryl]hydrogen phosphate), or bronchitol (inhaled formulation of mannitol).

In another embodiment, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In another embodiment, the additional agent is a CFTR modulator other than Compound 1, Solvate Form A or Compound 1, HCl Salt Form A, i.e., an agent that has the effect of modulating CFTR activity. Exemplary such agents include ataluren ("PTC124®"; 3-[5-(2-fluorophenyl)-1,2,4-oxadiazol-3-yl]benzoic acid), sinapultide, lancovutide, depelestat (a human recombinant neutrophil elastase inhibitor), and cobiprostone (7-{(2R,4aR,5R,7aR)-2-[(3S)-1,1-difluoro-3-methylpentyl]-2-hydroxy-6-oxooctahydrocyclopenta[b]pyran-5-yl}heptanoic acid).

In another embodiment, the additional agent is a nutritional agent. Exemplary nutritional agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

In another embodiment, the additional agent is a compound selected from gentamicin, curcumin, cyclophosphamide, 4-phenylbutyrate, miglustat, felodipine, nimodipine, Philoxin B, geniestein, Apigenin, cAMP/cGMP modulators such as rolipram, sildenafil, milrinone, tadalafil, amrinone, isoproterenol, albuterol, and almeterol, deoxyspergualin, HSP 90 inhibitors, HSP 70 inhibitors, proteosome inhibitors such as epoxomicin, lactacystin, etc.

In another embodiment, the additional agent is a compound disclosed in WO 2004028480, WO 2004110352, WO 2005094374, WO 2005120497, or WO 2006101740.

In another embodiment, the additional agent is a benzo(c) quinolizinium derivative that exhibits CFTR modulation activity or a benzopyran derivative that exhibits CFTR modulation activity.

In another embodiment, the additional agent is a compound disclosed in U.S. Pat. No. 7,202,262, U.S. Pat. No. 6,992,096, US20060148864, US20060148863, US20060035943, US20050164973, WO2006110483, WO2006044456, WO2006044682, WO2006044505, WO2006044503, WO2006044502, or WO2004091502.

In another embodiment, the additional agent is a compound disclosed in WO2004080972, WO2004111014, WO2005035514, WO2005049018, WO2006099256, WO2006127588, or WO2007044560.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Compound 1, Solvate Form A or Compound 1, HCl Salt Form A, as described herein, or pharmaceutically acceptable compositions thereof, may also be incorporated into compositions for coating an implantable medical device, such as prostheses, artificial valves, vascular grafts, stents, and catheters. Accordingly, the present invention, in another aspect, includes a composition for coating an implantable device comprising Compound 1, Solvate Form A or Compound 1, HCl Salt Form A, as described herein, or pharmaceutically acceptable compositions thereof, and in classes and subclasses herein, and a carrier suitable for coating said implantable device. In still another aspect, the present invention includes an implantable device coated with a composition comprising Compound 1, Solvate Form A or Compound 1, HCl Salt Form A as described herein, or pharmaceutically acceptable compositions thereof, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. Optionally, the coatings may be further covered by a suitable topcoat of fluorosilicone, polysaccharides, polyethylene glycol, phospholipids, or combinations thereof to impart controlled release characteristics in the composition.

In order that the invention described herein may be more fully understood, the following examples are set forth. It should be understood that these examples are for illustrative purposes only and are not to be construed as limiting this invention in any manner.

EXAMPLES

Methods & Materials

Differential Scanning Calorimetry (DSC)

The Differential scanning calorimetry (DSC) data for Compound 1, Solvate Form A were collected using a DSC Q100 V9.6 Build 290 (TA Instruments, New Castle, Del.). Temperature was calibrated with indium, and heat capacity was calibrated with sapphire. Samples of 3-6 mg were weighed into aluminum pans that were crimped using lids with 1 pin hole. The samples were scanned from 25° C. to 350° C. at a heating rate of 1.0° C./min and with a nitrogen gas purge of 50 ml/min. Data were collected by Thermal Advantage Q Series™ version 2.2.0.248 software and analyzed by Universal Analysis software version 4.1D (TA Instruments, New Castle, Del.). The reported numbers represent single analyses.

Jet Milling Description

Unmicronized Compound 1, Solvate Form A or Compound 1, HCl Salt Form A is sieved to de-lump it prior to placing it into the jet mill hopper. All sieves are disposable and received a wipe prior to use. Unmicronized Compound 1, Solvate Form A or Compound 1, HCl Salt Form A is added to the jet mill hopper at a controlled feeding rate using compressed nitrogen gas. The gas pressure range is 40-45/45-70 (Venturi/Mill) PSI and the feeding rate range is 0.5-1.6 Kg/Hour. The Compound 1, Solvate Form A or Compound 1, HCl Salt Form A is micronized in the mill through particle-particle and particle-wall collisions and the processed Compound 1, Solvate Form A or Compound 1, HCl Salt Form A is emptied into the micronized product containers. It is believed that one of ordinary skill in the art may also achieve Compound 1, Solvate Form A or Compound 1, HCl Salt Form A with a favorable particle size through pin milling based in part on the conditions described above.

XRPD (X-Ray Powder Diffraction)

X-Ray diffraction (XRD) data were collected on either a Bruker D8 DISCOVER or Bruker APEX II powder diffractometer. The Bruker D8 DISCOVER Diffractomer with HI-STAR 2-dimensional detector and a flat graphite monochromator. Cu sealed tube with K-alpha radiation was used at 40 kV, 35 mA. The samples were placed on zero-background silicon wafers at 25° C. For each sample, two data frames were collected at 120 seconds each at 2 different $\theta_2$ angles: 8° and 26°. The data were integrated with GADDS software and merged with DIFFRACT$^{plus}$EVA software. Uncertainties for the reported peak positions are ±0.2 degrees. equipped with sealed tube Cu Kα source and an Apex II CCD detector.

The Bruker II powder diffractomer was equipped with a sealed tube CuK source and an APEX II CCD detector. Structures were solved and refined using the SHELX program. (Sheldrick, G. M., Acta Cryst. (2008) A64, 112-122).

Vitride® (sodium bis(2-methoxyethoxy)aluminum hydride [or NaAlH$_2$(OCH$_2$CH$_2$OCH$_3$)$_2$], 65 wgt % solution in toluene) was purchased from Aldrich Chemicals.

2,2-Difluoro-1,3-benzodioxole-5-carboxylic acid was purchased from Saltigo (an affiliate of the Lanxess Corporation).

Anywhere in the present application where a name of a compound may not correctly describe the structure of the compound, the structure supersedes the name and governs.

Preparation of
(2,2-difluoro-1,3-benzodioxol-5-yl)-methanol

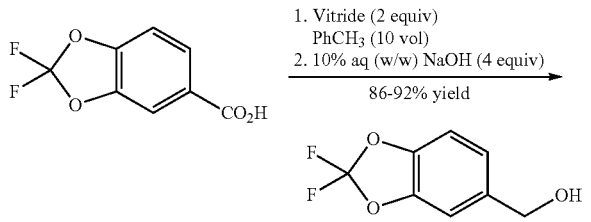

Commercially available 2,2-difluoro-1,3-benzodioxole-5-carboxylic acid (1.0 eq) was slurried in toluene (10 vol). Vitride® (2 eq) was added via addition funnel at a rate to maintain the temperature at 15 to 25° C. At the end of the addition, the temperature was increased to 40° C. for 2 hours (h), then 10% (w/w) aqueous (aq) NaOH (4.0 eq) was carefully added via addition funnel, maintaining the temperature at 40 to 50° C. After stirring for an additional 30 minutes (min), the layers were allowed to separate at 40° C. The organic phase was cooled to 20° C., then washed with water (2×1.5 vol), dried (Na$_2$SO$_4$), filtered, and concentrated to afford crude (2,2-difluoro-1,3-benzodioxol-5-yl)-methanol that was used directly in the next step.

Preparation of
5-chloromethyl-2,2-difluoro-1,3-benzodioxole

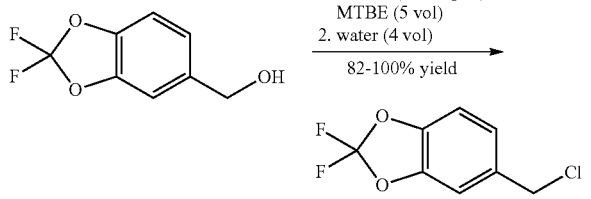

(2,2-difluoro-1,3-benzodioxol-5-yl)-methanol (1.0 eq) was dissolved in MTBE (5 vol). A catalytic amount of 4-(N, N-dimethyl)aminopyridine (DMAP) (1 mol %) was added and SOCl$_2$ (1.2 eq) was added via addition funnel. The SOCl$_2$ was added at a rate to maintain the temperature in the reactor at 15 to 25° C. The temperature was increased to 30° C. for 1 hour, and then was cooled to 20° C. Water (4 vol) was added via addition funnel while maintaining the temperature at less than 30° C. After stirring for an additional 30 minutes, the layers were allowed to separate. The organic layer was stirred, and 10% (w/v) aq NaOH (4.4 vol) was added. After stirring for 15 to 20 minutes, the layers were allowed to separate. The organic phase was then dried (Na$_2$SO$_4$), filtered, and concentrated to afford crude 5-chloromethyl-2,2-difluoro-1,3-benzodioxole that was used directly in the next step.

Preparation of
(2,2-difluoro-1,3-benzodioxol-5-yl)-acetonitrile

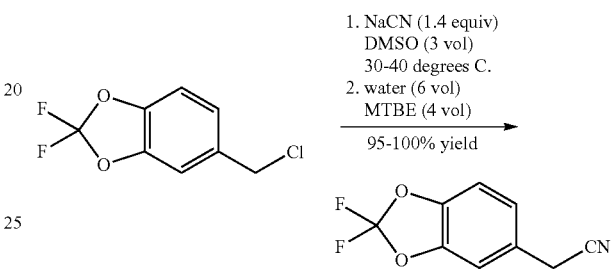

A solution of 5-chloromethyl-2,2-difluoro-1,3-benzodioxole (1 eq) in DMSO (1.25 vol) was added to a slurry of NaCN (1.4 eq) in DMSO (3 vol), while maintaining the temperature between 30 to 40° C. The mixture was stirred for 1 hour, and then water (6 vol) was added, followed by methyl tert-butyl ether (MTBE) (4 vol). After stirring for 30 minutes, the layers were separated. The aqueous layer was extracted with MTBE (1.8 vol). The combined organic layers were washed with water (1.8 vol), dried (Na$_2$SO$_4$), filtered, and concentrated to afford crude (2,2-difluoro-1,3-benzodioxol-5-yl)-acetonitrile (95%) that was used directly in the next step.

Synthesis of (2,2-difluoro-1,3-benzodioxol-5-yl)-1-ethylacetate-acetonitrile

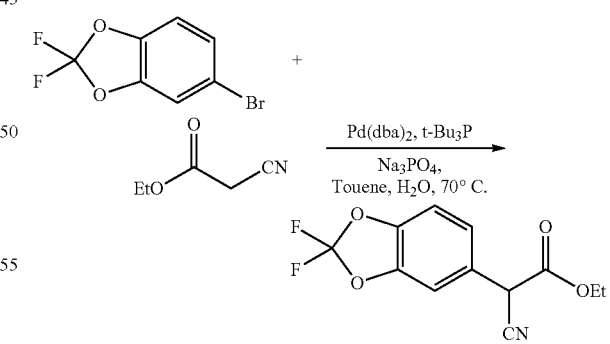

A reactor was purged with nitrogen and charged with toluene (900 mL). The solvent was degassed via nitrogen sparge for no less than 16 hours. To the reactor was then charged Na$_3$PO$_4$ (155.7 g, 949.5 mmol), followed by bis(dibenzylideneacetone) palladium (0) (7.28 g, 12.66 mmol). A 10% w/w solution of tert-butylphosphine in hexanes (51.23 g, 25.32 mmol) was charged over 10 minutes at 23° C. from a nitrogen purged addition funnel. The mixture was allowed to stir for 50 minutes, at which time 5-bromo-2,2-difluoro-1,3-benzodioxole (75 g, 316.5 mmol) was added over 1 minute. After stirring for an additional 50 minutes, the mixture was charged with ethyl cyanoacetate (71.6 g, 633.0 mmol) over 5 minutes, followed by water (4.5 mL) in one portion. The mixture was heated to 70° C. over 40 minutes and analyzed by HPLC every 1 to 2 hours for the percent conversion of the reactant to the product. After complete conversion was observed (typically 100% conversion after 5 to 8 hours), the mixture was cooled to 20 to 25° C. and filtered through a celite pad. The celite pad was rinsed with toluene (2×450 mL), and the combined organics were concentrated to 300 mL under vacuum at 60 to 65° C. The concentrate was charged with DMSO (225 mL) and concentrated under vacuum at 70 to 80° C. until active distillation of the solvent ceased. The solution was cooled to 20 to 25° C. and diluted to 900 mL with DMSO in preparation for Step 2. $^1$H NMR (500 MHz, CDCl$_3$) δ 7.16-7.10 (m, 2H), 7.03 (d, J=8.2 Hz, 1H), 4.63 (s, 1H), 4.19 (m, 2H), 1.23 (t, J=7.1 Hz, 3H).

Synthesis of
(2,2-difluoro-1,3-benzodioxol-5-yl)-acetonitrile

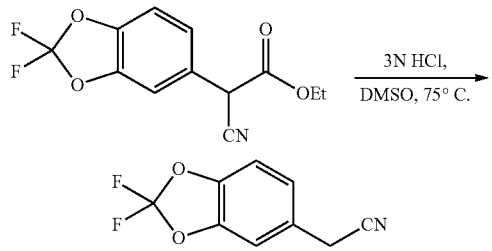

The DMSO solution of (2,2-difluoro-1,3-benzodioxol-5-yl)-1-ethylacetate-acetonitrile from above was charged with 3 N HCl (617.3 mL, 1.85 mol) over 20 minutes while maintaining an internal temperature less than 40° C. The mixture was then heated to 75° C. over 1 hour and analyzed by HPLC every 1 to 2 hour for percent conversion. When a conversion of greater than 99% was observed (typically after 5 to 6 hours), the reaction was cooled to 20 to 25° C. and extracted with MTBE (2×525 mL), with sufficient time to allow for complete phase separation during the extractions. The combined organic extracts were washed with 5% NaCl (2×375 mL). The solution was then transferred to equipment appropriate for a 1.5 to 2.5 Torr vacuum distillation that was equipped with a cooled receiver flask. The solution was concentrated under vacuum at less than 60° C. to remove the solvents. (2,2-Difluoro-1,3-benzodioxol-5-yl)-acetonitrile was then distilled from the resulting oil at 125 to 130° C. (oven temperature) and 1.5 to 2.0 Torr. (2,2-Difluoro-1,3-benzodioxol-5-yl)-acetonitrile was isolated as a clear oil in 66% yield from 5-bromo-2,2-difluoro-1,3-benzodioxole (2 steps) and with an HPLC purity of 91.5% AUC (corresponds to a w/w assay of 95%). $^1$H NMR (500 MHz, DMSO) δ 7.44 (br s, 1H), 7.43 (d, J=8.4 Hz, 1H), 7.22 (dd, J=8.2, 1.8 Hz, 1H), 4.07 (s, 2H).

Preparation of (2,2-difluoro-1,3-benzodioxol-5-yl)-cyclopropanecarbonitrile

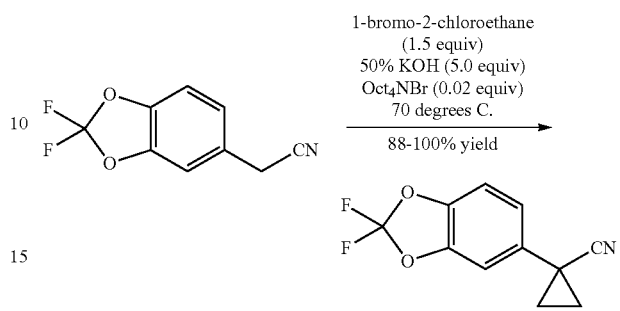

A mixture of (2,2-difluoro-1,3-benzodioxol-5-yl)-acetonitrile (1.0 eq), 50 wt % aqueous KOH (5.0 eq) 1-bromo-2-chloroethane (1.5 eq), and Oct$_4$NBr (0.02 eq) was heated at 70° C. for 1 hour. The reaction mixture was cooled, then worked up with MTBE and water. The organic phase was washed with water and brine. The solvent was removed to afford (2,2-difluoro-1,3-benzodioxol-5-yl)-cyclopropanecarbonitrile.

Preparation of 1-(2,2-difluoro-1,3-benzodioxol-5-yl)-cyclopropanecarboxylic acid

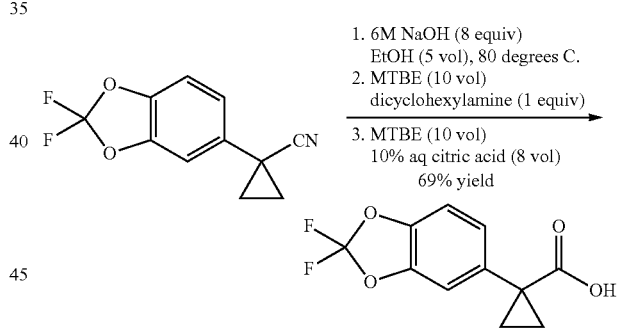

(2,2-difluoro-1,3-benzodioxol-5-yl)-cyclopropanecarbonitrile was hydrolyzed using 6 M NaOH (8 equiv) in ethanol (5 vol) at 80° C. overnight. The mixture was cooled to room temperature, and the ethanol was evaporated under vacuum. The residue was taken up in water and MTBE, 1 M HCl was added, and the layers were separated. The MTBE layer was then treated with dicyclohexylamine (DCHA) (0.97 equiv). The slurry was cooled to 0° C., filtered, and washed with heptane to give the corresponding DCHA salt. The salt was taken into MTBE and 10% citric acid and stirred until all the solids had dissolved. The layers were separated, and the MTBE layer was washed with water and brine. A solvent swap to heptane followed by filtration gave 1-(2,2-difluoro-1,3-benzodioxol-5-yl)-cyclopropanecarboxylic acid after drying in a vacuum oven at 50° C. overnight.

Preparation of 1-(2,2-difluoro-1,3-benzodioxol-5-yl)-cyclopropanecarbonyl chloride

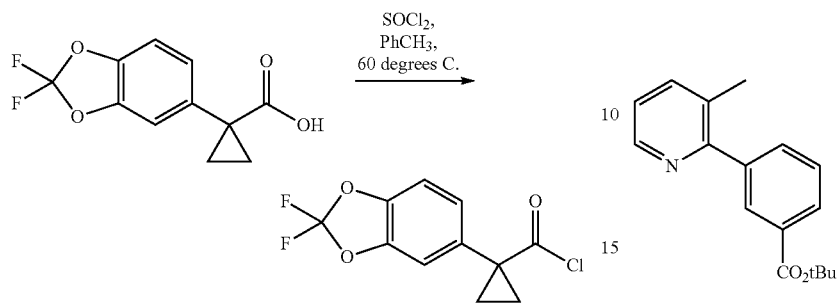

1-(2,2-difluoro-1,3-benzodioxol-5-yl)-cyclopropanecarboxylic acid (1.2 eq) was slurried in toluene (2.5 vol), and the mixture was heated to 60° C. SOCl₂ (1.4 eq) was added via addition funnel. The toluene and SOCl₂ were distilled from the reaction mixture after 30 minutes. Additional toluene (2.5 vol) was added, and the resulting mixture was distilled again, leaving the product acid chloride as an oil, which was used without further purification.

Preparation of tert-butyl-3-(3-methylpyridin-2-yl)benzoate

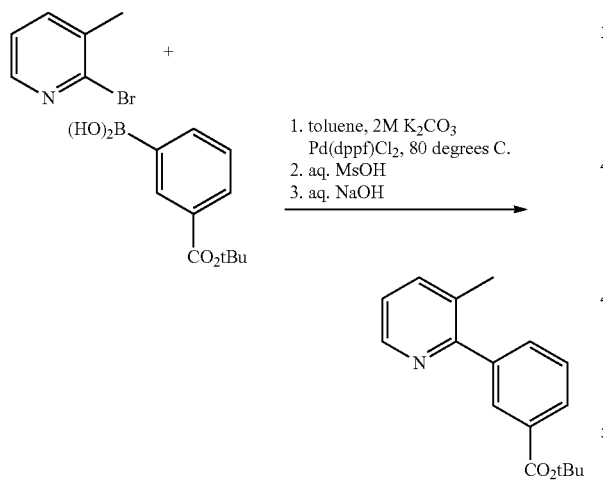

2-Bromo-3-methylpyridine (1.0 eq) was dissolved in toluene (12 vol). K₂CO₃ (4.8 eq) was added, followed by water (3.5 vol). The resulting mixture was heated to 65° C. under a stream of N₂ for 1 hour. 3-(t-Butoxycarbonyl)phenylboronic acid (1.05 eq) and Pd(dppf)Cl₂.CH₂Cl₂ (0.015 eq) were then added, and the mixture was heated to 80° C. After 2 hours, the heat was turned off, water was added (3.5 vol), and the layers were allowed to separate. The organic phase was then washed with water (3.5 vol) and extracted with 10% aqueous methanesulfonic acid (2 eq MsOH, 7.7 vol). The aqueous phase was made basic with 50% aqueous NaOH (2 eq) and extracted with EtOAc (8 vol). The organic layer was concentrated to afford crude tert-butyl-3-(3-methylpyridin-2-yl)benzoate (82%) that was used directly in the next step.

Preparation of 2-(3-(tert-butoxycarbonyl)phenyl)-3-methylpyridine-1-oxide

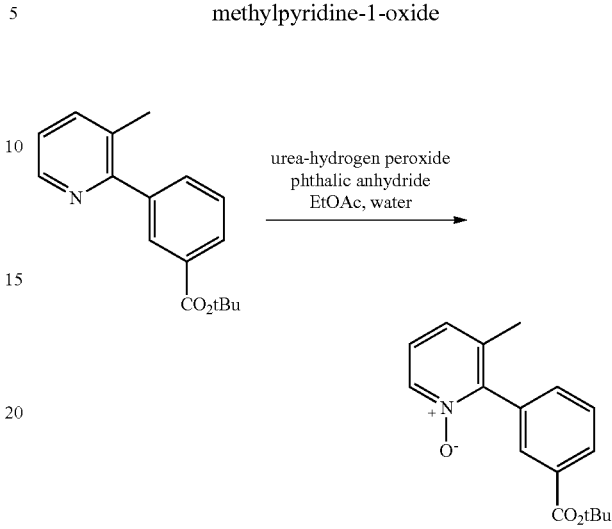

tert-Butyl-3-(3-methylpyridin-2-yl)benzoate (1.0 eq) was dissolved in EtOAc (6 vol). Water (0.3 vol) was added, followed by urea-hydrogen peroxide (3 eq). Phthalic anhydride (3 eq) was then added portionwise to the mixture as a solid at a rate to maintain the temperature in the reactor below 45° C. After completion of the phthalic anhydride addition, the mixture was heated to 45° C. After stirring for an additional 4 hours, the heat was turned off. 10% w/w aqueous Na₂SO₃ (1.5 eq) was added via addition funnel. After completion of Na₂SO₃ addition, the mixture was stirred for an additional 30 minutes, and the layers separated. The organic layer was stirred, and 10% wt/wt aqueous. Na₂CO₃ (2 eq) was added. After stirring for 30 minutes, the layers were allowed to separate. The organic phase was washed 13% w/v aq NaCl. The organic phase was then filtered and concentrated to afford crude 2-(3-(tert-butoxycarbonyl)phenyl)-3-methylpyridine-1-oxide (95%) that was used directly in the next step.

Preparation of tert-butyl-3-(6-amino-3-methylpyridin-2-yl)benzoate

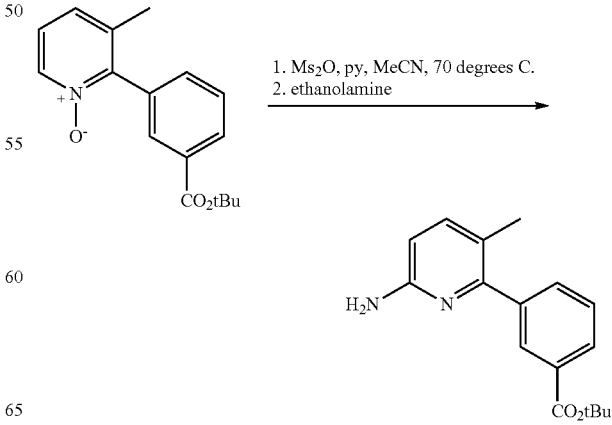

A solution of 2-(3-(tert-butoxycarbonyl)phenyl)-3-methylpyridine-1-oxide (1 eq) and pyridine (4 eq) in acetonitrile (8 vol) was heated to 70° C. A solution of methanesulfonic anhydride (1.5 eq) in MeCN (2 vol) was added over 50 minutes via addition funnel while maintaining the temperature at less than 75° C. The mixture was stirred for an additional 0.5 hours after complete addition. The mixture was then allowed to cool to ambient temperature. Ethanolamine (10 eq) was added via addition funnel. After stirring for 2 hours, water (6 vol) was added, and the mixture was cooled to 10° C. After stirring for 3 hours, the solid was collected by filtration and washed with water (3 vol), 2:1 acetonitrile/water (3 vol), and acetonitrile (2×1.5 vol). The solid was dried to constant weight (less than 1% difference) in a vacuum oven at 50° C. with a slight $N_2$ bleed to afford tert-butyl-3-(6-amino-3-methylpyridin-2-yl)benzoate as a red-yellow solid (53% yield).

(2,2-difluorobenzo[d][1,3]dioxol-5-yl)cyclopropanecarboxamido)-3-methylpyridin-2-yl)-t-butylbenzoate (quantitative crude yield). Acetonitrile (3 vol based on crude product) was added and distilled until crystallization occurred. Water (2 vol based on crude product) was added, and the mixture stirred for 2 hours. The solid was collected by filtration, washed with 1:1 (by volume) acetonitrile/water (2×1 volumes based on crude product), and partially dried on the filter under vacuum. The solid was dried to a constant weight (less than 1% difference) in a vacuum oven at 60° C. with a slight $N_2$ bleed to afford 3-(6-(1-(2,2-difluorobenzo[d][1,3]dioxol-5-yl)cyclopropanecarboxamido)-3-methylpyridin-2-yl)-t-butylbenzoate as a brown solid.

Preparation of 3-(6-(1-(2,2-difluorobenzo[d][1,3]dioxol-5-yl)cyclopropanecarboxamido)-3-methylpyridin-2-yl)benzoic acid.HCL salt

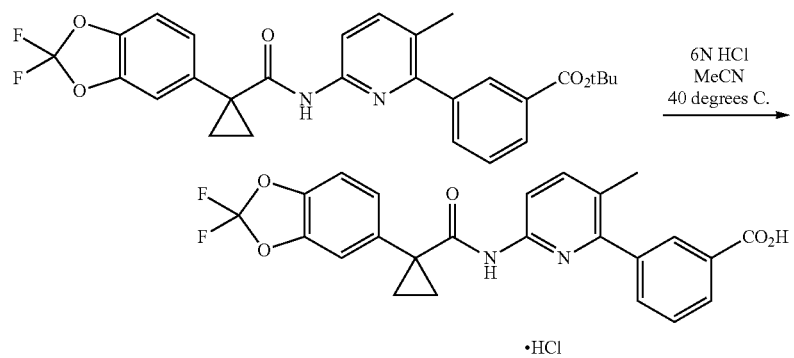

Preparation of 3-(6-(1-(2,2-difluorobenzo[d][1,3]dioxol-5-yl)-cyclopropanecarboxamido)-3-methylpyridin-2-yl)-t-butylbenzoate

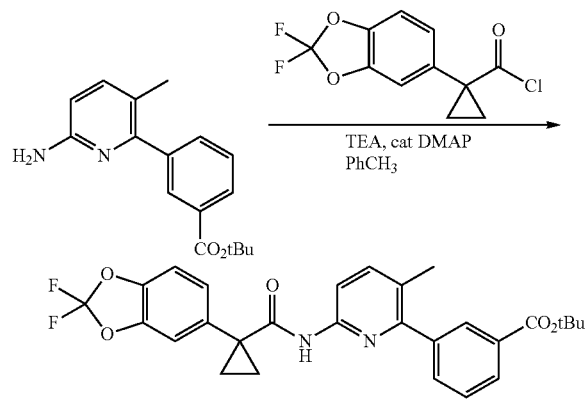

The crude acid chloride described above was dissolved in toluene (2.5 vol based on acid chloride) and added via addition funnel to a mixture of tert-butyl-3-(6-amino-3-methylpyridin-2-yl)benzoate (1 eq), DMAP, (0.02 eq), and triethylamine (3.0 eq) in toluene (4 vol based on tert-butyl-3-(6-amino-3-methylpyridin-2-yl)benzoate). After 2 hours, water (4 vol based on tert-butyl-3-(6-amino-3-methylpyridin-2-yl)benzoate) was added to the reaction mixture. After stirring for 30 minutes, the layers were separated. The organic phase was then filtered and concentrated to afford a thick oil of 3-(6-(1-

To a slurry of 3-(6-(1-(2,2-difluorobenzo[d][1,3]dioxol-5-yl)cyclopropanecarboxamido)-3-methylpyridin-2-yl)-t-butylbenzoate (1.0 eq) in MeCN (3.0 vol) was added water (0.83 vol) followed by concentrated aqueous HCl (0.83 vol). The mixture was heated to 45±5° C. After stirring for 24 to 48 hours, the reaction was complete, and the mixture was allowed to cool to ambient temperature. Water (1.33 vol) was added and the mixture stirred. The solid was collected by filtration, washed with water (2×0.3 vol), and partially dried on the filter under vacuum. The solid was dried to a constant weight (less than 1% difference) in a vacuum oven at 60° C. with a slight $N_2$ bleed to afford 3-(6-(1-(2,2-difluorobenzo[d][1,3]dioxol-5-yl)cyclopropanecarboxamido)-3-methylpyridin-2-yl)benzoic acid.HCl as an off-white solid.

Preparation of 3-(6-(1-(2,2-difluorobenzo[d][1,3]dioxol-5-yl)cyclopropanecarboxamido)-3-methylpyridin-2-yl)benzoic acid, Form I, Method A

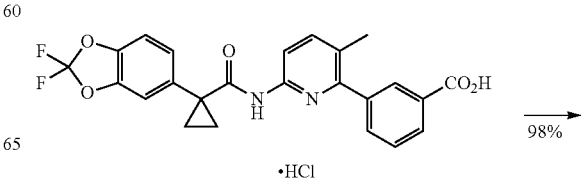

-continued

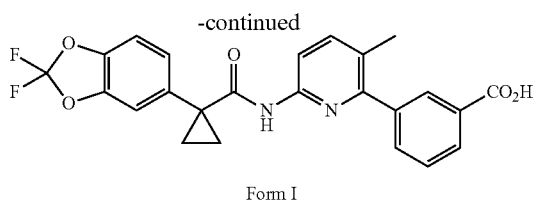

Form I

A slurry of 3-(6-(1-(2,2-difluorobenzo[d][1,3]dioxol-5-yl) cyclopropanecarboxamido)-3-methylpyridin-2-yl)benzoic acid.HCl (1 eq) in water (10 vol) was stirred at ambient temperature. A sample was taken after stirring for 24 hours. The sample was filtered, and the solid was washed with water (2 times). The solid sample was submitted for DSC analysis. When DSC analysis indicated complete conversion to Form I, the solid was collected by filtration, washed with water (2×1.0 vol), and partially dried on a filter under vacuum. The solid was then dried to a constant weight (less than 1% difference) in a vacuum oven at 60° C. with a slight $N_2$ bleed to afford Form I as an off-white solid (98% yield). $^1$H NMR (400 MHz, DMSO-d6) 9.14 (s, 1H), 7.99-7.93 (m, 3H), 7.80-7.78 (m, 1H), 7.74-7.72 (m, 1H), 7.60-7.55 (m, 2H), 7.41-7.33 (m, 2H), 2.24 (s, 3H), 1.53-1.51 (m, 2H), 1.19-1.17 (m, 2H).

Preparation of 3-(6-(1-(2,2-difluorobenzo[d][1,3] dioxol-5-yl)cyclopropanecarboxamido)-3-methylpyridin-2-yl)benzoic acid, Form I, Method B

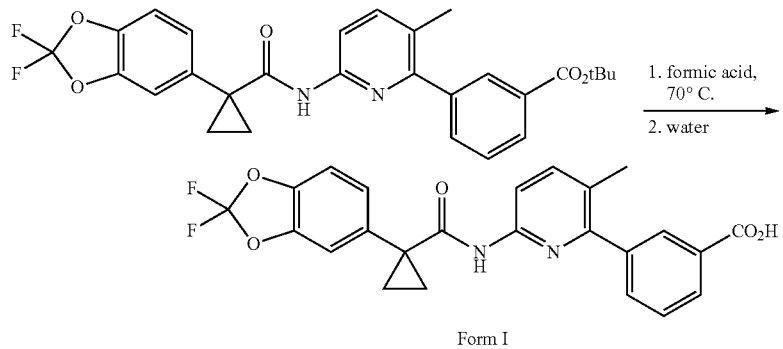

Form I

A solution of 3-(6-(1-(2,2-difluorobenzo[d][1,3]dioxol-5-yl)cyclopropanecarboxamido)-3-methylpyridin-2-yl)-t-butylbenzoate (1.0 eq) in formic acid (3.0 vol) was heated with stirring to 70±10° C. for 8 hours. The reaction was deemed complete when no more than 1.0% AUC by chromatographic methods of 3-(6-(1-(2,2-difluorobenzo[d][1,3]dioxol-5-yl) cyclopropanecarboxamido)-3-methylpyridin-2-yl)-t-butylbenzoate) remained. The mixture was allowed to cool to ambient. The solution was added to water (6 vol), heated at 50° C., and stirred. The mixture was then heated to 70±10° C. until the level of 3-(6-(1-(2,2-difluorobenzo[d][1,3]dioxol-5-yl)cyclopropanecarboxamido)-3-methylpyridin-2-yl)-t-butylbenzoate was no more than 0.8% (AUC). The solid was collected by filtration, washed with water (2×3 vol), and partially dried on the filter under vacuum. The solid was dried to a constant weight (less than 1% difference) in a vacuum oven at 60° C. with a slight $N_2$ bleed to afford Compound 1 in Form I as an off-white solid.

Preparation of Compound 1, Solvate Form A from Compound 1, Form I

Compound 1, Form I (approximately 30 mg) was slurried in 500 μL of an appropriate solvent (for example, methanol, ethanol, acetone, 2-propanol, acetonitrile, tetrahydrofuran, methyl acetate, 2-butanone, ethyl formate, and -methyl tetrahydrofuran) for two days. The slurry was then filtered centrifugally or under vacuum and was left to dry at ambient temperature overnight to yield Compound 1, Solvate Form A.

Figure 13:
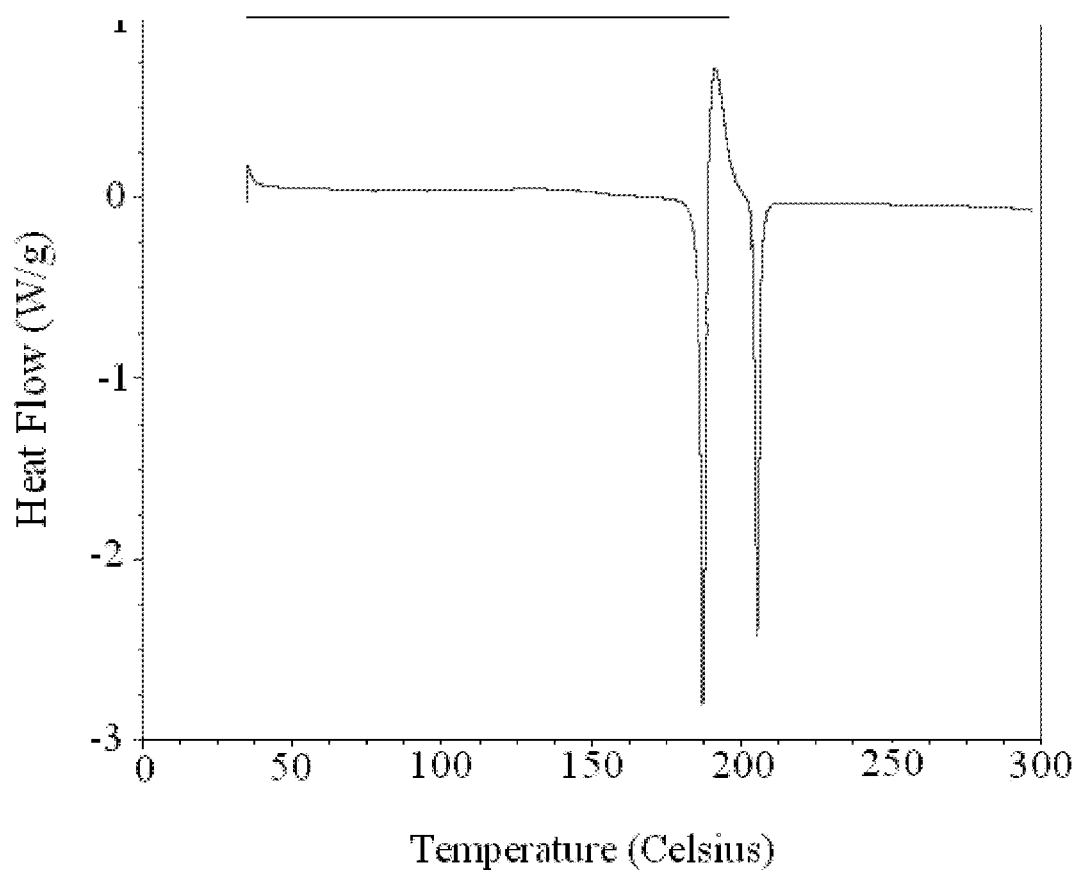
FIG. 13 is a differential scanning calorimetry (DSC) trace of Compound 1, Acetone Solvate Form A.

The DSC trace of Compound 1, Acetone Solvate Form A is shown in FIG. 13, showing two phase transitions. The melting point for Compound 1, Acetone Solvate Form A occurs at about 188° C. and 205° C.

An actual X-ray powder diffraction pattern of Compound 1, Solvate Form A is shown in FIG. 1. Table 2 lists the actual peaks for FIG. 1 in descending order of relative intensity. Table 2.

TABLE 2

| 2θ Angle [degrees] | Relative Intensity [%] |
|---|---|
| 21.70 | 100.0 |
| 8.98 | 65.5 |
| 11.04 | 57.4 |
| 18.16 | 55.9 |
| 23.06 | 55.4 |
| 20.63 | 53.1 |
| 22.22 | 50.2 |

TABLE 2-continued

| 2θ Angle [degrees] | Relative Intensity [%] |
|---|---|
| 18.57 | 49.1 |
| 16.66 | 47.2 |
| 19.86 | 35.0 |

Figure 16:
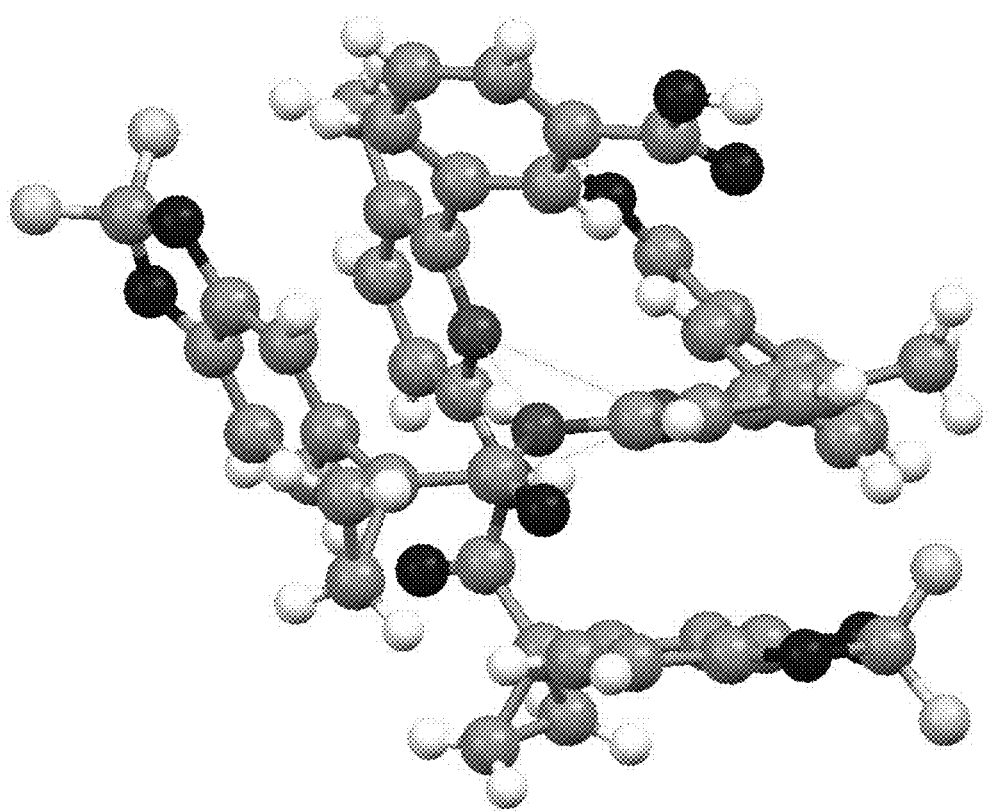
FIG. 16 is a conformational image of Compound 1, Solvate Form A based on single crystal X-ray analysis as a dimer.
Figure 17:
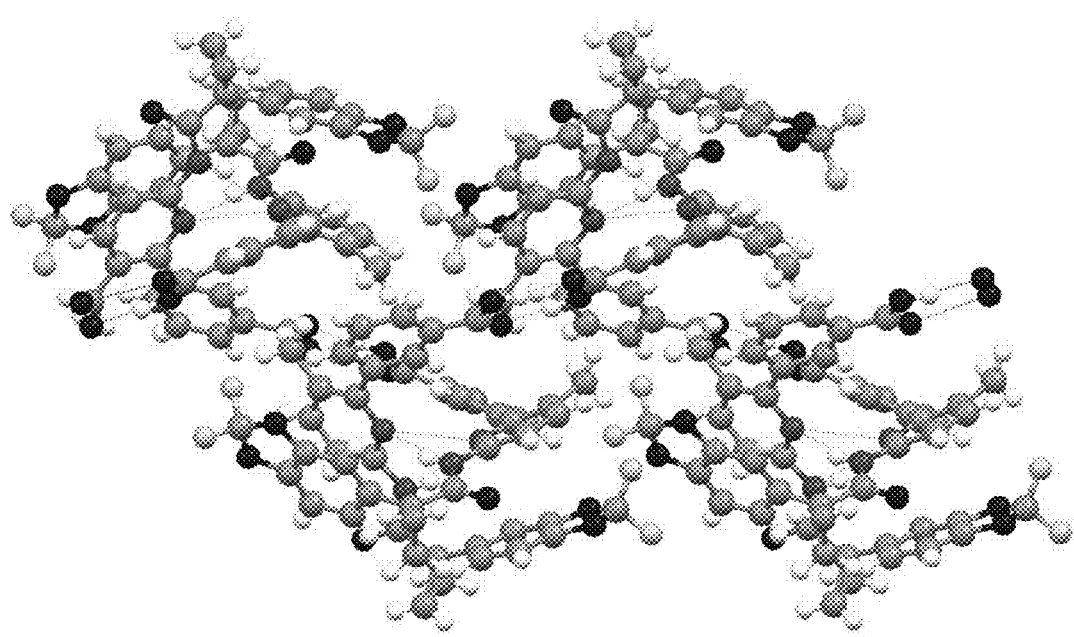
FIG. 17 is a conformational image of Compound 1, Solvate Form A showing hydrogen bonding between carboxylic acid groups based on single crystal X-ray analysis.
Figure 18:
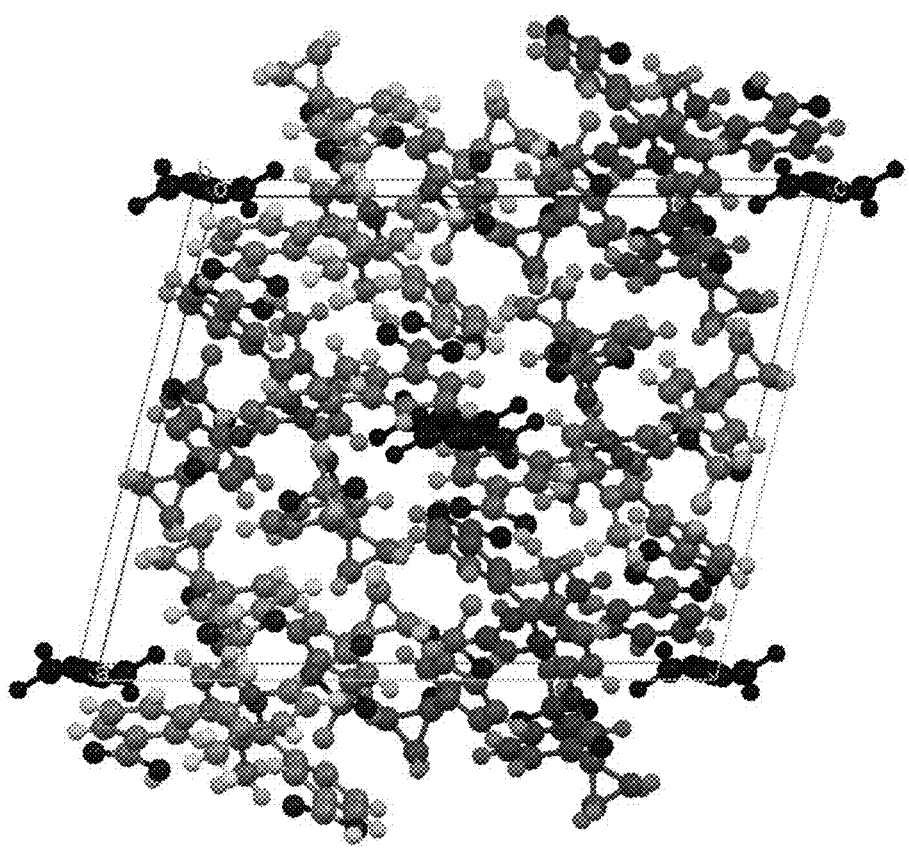
FIG. 18 is a conformational image of Compound 1, Solvate Form A showing acetone as the solvate based on single crystal X-ray analysis.

Conformational depictions of Compound 1, Acetone Solvate Form A based on single crystal X-ray analysis are shown in FIGS. 15-18. FIG. 15 shows a conformational image of Compound 1, Acetone Solvate Form A, based on single crystal X-ray analysis. FIG. 16 provides a conformational image of Compound 1, Acetone Solvate Form A as a dimer showing hydrogen bonding between the carboxylic acid groups based on single X-ray crystal analysis. FIG. 17 provides a conformational image of a tetramer of Compound 1, Acetone Solvate Form A. FIG. 18 provides a confirmation of Compound 1, Acetone Solvate Form A, based on single crystal X-ray analysis. The stoichiometry between Compound 1, Solvate Form A and acetone is approximately 4.4:1 (4.48:1 calculated from $^1$H NMR; 4.38:1 from X-ray). The crystal structure reveals a packing of the molecules where there are two voids or pockets per unit cell, or 1 void per host molecule. In the acetone solvate, approximately 92 percent of voids are occupied by acetone molecules. Compound 1, Solvate Form A is a monoclinic P2$_1$/n space group with the following unit cell dimensions: a=16.5235(10) Å, b=12.7425(8) Å, c=20.5512 (13) Å, α=90°, β=103.736(4)°, γ=90°, V=4203.3(5) Å$^3$, =4. The density of Compound 1 in Compound 1, Solvate Form A calculated from structural data is 1.430/cm$^3$ at 100 K.

Figure 22:
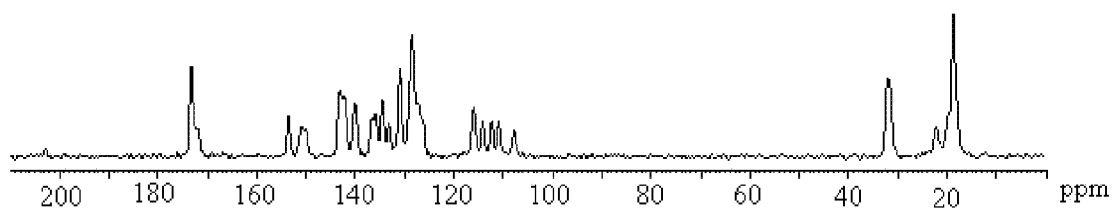
FIG. 22 is a solid state $^{13}C$ NMR spectrum (15.0 kHz spinning) of Compound 1, Acetone Solvate Form A.

A solid state $^{13}$C NMR spectrum of Compound 1, Acetone Solvate Form A is shown in FIG. 22. Table 3 provides chemical shifts of the relevant peaks.

TABLE 3

Compound 1, Acetone Solvate Form A
$^{13}$C Chem. Shifts

| Peak # | F1 [ppm] | Intensity |
|---|---|---|
| 1 | 202.8 | 6.05 |
| 2 | 173.3 | 62.66 |
| 3 | 171.9 | 20.53 |
| 4 | 153.5 | 28.41 |
| 5 | 150.9 | 21.68 |
| 6 | 150.1 | 19.49 |
| 7 | 143.2 | 45.74 |
| 8 | 142.3 | 42.68 |
| 9 | 140.1 | 37.16 |
| 10 | 136.6 | 26.82 |
| 11 | 135.9 | 30.1 |
| 12 | 134.6 | 39.39 |
| 13 | 133.2 | 23.18 |
| 14 | 131.0 | 60.92 |
| 15 | 128.5 | 84.58 |
| 16 | 116.0 | 34.64 |
| 17 | 114.2 | 23.85 |
| 18 | 112.4 | 25.3 |
| 19 | 110.9 | 24.12 |
| 20 | 107.8 | 18.21 |
| 21 | 32.0 | 54.41 |
| 22 | 22.2 | 20.78 |
| 23 | 18.8 | 100 |

Figure 23:
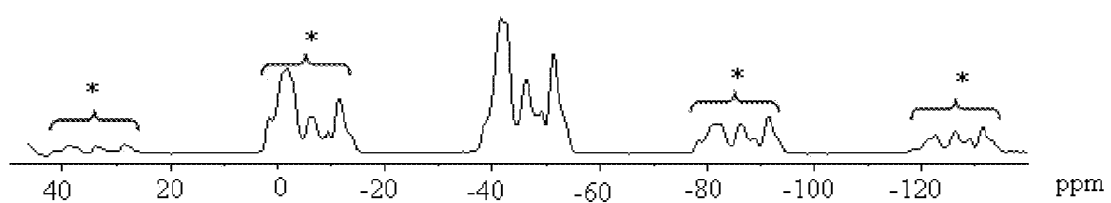
FIG. 23 is a solid state $^{19}F$ NMR spectrum (12.5 kHz spinning) of Compound 1, Acetone Solvate Form A.

A solid state $^{19}$F NMR spectrum of Compound 1, Acetone Solvate Form A is shown in FIG. 23. Peaks with an asterisk denote spinning side bands. Table 4 provides chemical shifts of the relevant peaks.

TABLE 4

Compound 1, Acetone Solvate Form A
$^{19}$F Chem. Shifts

| Peak # | F1 [ppm] | Intensity |
|---|---|---|
| 1 | −41.6 | 12.5 |
| 2 | −46.4 | 6.77 |
| 3 | −51.4 | 9.05 |

Preparation of Compound 1, HCl Salt Form A.

Colorless crystals of Compound 1, HCl Salt Form A was obtained by slow evaporation from a concentrated solution of the HCL salt of compound 1 in ethanol. A crystal with dimensions of 0.30×⅕×0.15 mm was selected, cleaned using mineral oil, mounted on a MicroMount, and centered on a Bruker APEXII diffractometer. Three batches of 40 frames separated in reciprocal space were obtained to provide an orientation matrix and initial cell parameters. Final cell parameters were obtained and refined based on the full data set.

FIG. 19 provides a conformational image of Compound 1, HCl Salt Form A as a dimer, based on single crystal analysis. FIG. 20 provides a packing diagram of Compound 1, HCl Salt Form A, based on single crystal analysis. An X-ray diffraction pattern of Compound 1, HCl Salt Form A calculated from the crystal structure is shown in FIG. 21. Table 5 contains the calculated peaks for FIG. 21 in descending order of relative intensity.

TABLE 5

| 2θ [degrees] | Relative Intensity [%] |
|---|---|
| 8.96 | 100.00 |
| 17.51 | 48.20 |
| 18.45 | 34.60 |
| 10.33 | 32.10 |
| 16.01 | 18.90 |
| 11.94 | 18.40 |
| 8.14 | 16.20 |
| 10.10 | 13.90 |
| 16.55 | 13.30 |
| 9.54 | 10.10 |
| 16.55 | 13.30 |

Assays

Assays for Detecting and Measuring ΔF508-CFTR Correction Properties of Compounds Membrane Potential Optical Methods for Assaying ΔF508-CFTR Modulation Properties of Compounds The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential (V$_m$) cause the negatively charged DiSBAC$_2$(3) to redistribute across the plasma membrane, and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

1. Identification of Correction Compounds

To identify small molecules that correct the trafficking defect associated with ΔF508-CFTR, a single-addition HTS assay format was developed. The cells were incubated in serum-free medium for 16 hours at 37° C. in the presence or absence (negative control) of test compound. As a positive control, cells plated in 384-well plates were incubated for 16 hours at 27° C. to "temperature-correct" ΔF508-CFTR. The cells were subsequently rinsed three times with Krebs Ringers solution and loaded with the voltage-sensitive dyes. To activate ΔF508-CFTR, 10 μM forskolin and the CFTR potentiator, genistein (20 μM), were added along with Cl⁻-free medium to each well. The addition of Cl⁻-free medium promoted Cl⁻ efflux in response to ΔF508-CFTR activation, and the resulting membrane depolarization was optically monitored using the FRET-based voltage-sensor dyes.

2. Identification of Potentiator Compounds

To identify potentiators of ΔF508-CFTR, a double-addition HTS assay format was developed. During the first addition, a Cl⁻-free medium with or without test compound was added to each well. After 22 seconds, a second addition of CF-free medium containing 2 to 10 µM forskolin was added to activate ΔF508-CFTR. The extracellular Cl⁻ concentration following both additions was 28 mM, which promoted Cl⁻ efflux in response to ΔF508-CFTR activation and the resulting membrane depolarization was optically monitored using the FRET-based voltage-sensor dyes.

3. Solutions

Bath Solution #1 (in mM): NaCl 160, KCl 4.5, $CaCl_2$ 2, $MgCl_2$ 1, HEPES 10, pH 7.4 with NaOH.

Chloride-free bath solution: Chloride salts in Bath Solution #1 are substituted with gluconate salts.

Prepared as a 10 mM stock solution in DMSO and stored at −20° C.

Prepared as a 10 mM stock in DMSO and stored at −20° C.

4. Cell Culture

NIH3T3 mouse fibroblasts stably expressing ΔF508-CFTR are used for optical measurements of membrane potential. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1×pen/strep, and 25 mM HEPES in 175 $cm^2$ culture flasks. For all optical assays, the cells were seeded at 30,000/well in 384-well matrigel-coated plates and cultured for 2 hours at 37° C. before culturing at 27° C. for 24 hours for the potentiator assay. For the correction assays, the cells are cultured at 27° C. or 37° C. with and without compounds for 16 to 24 hours.

Electrophysiological Assays for Assaying ΔF508-CFTR Modulation Properties of Compounds 1. Using Chamber Assay Chamber experiments were performed on polarized epithelial cells expressing ΔF508-CFTR to further characterize the ΔF508-CFTR modulators identified in the optical assays. $FRT^{\Delta F508-CFTR}$ epithelial cells grown on Costar Snapwell cell culture inserts were mounted in an Ussing chamber (Physiologic Instruments, Inc., San Diego, Calif.), and the monolayers were continuously short-circuited using a Voltage-clamp System (Department of Bioengineering, University of Iowa, Iowa, and, Physiologic Instruments, Inc., San Diego, Calif.). Transepithelial resistance was measured by applying a 2-mV pulse. Under these conditions, the FRT epithelia demonstrated resistances of 4 KΩ/$cm^2$ or more. The solutions were maintained at 27° C. and bubbled with air. The electrode offset potential and fluid resistance were corrected using a cell-free insert. Under these conditions, the current reflects the flow of Cl⁻ through ΔF508-CFTR expressed in the apical membrane. The $I_{SC}$ was digitally acquired using an MP100A-CE interface and AcqKnowledge software (v3.2.6; BIOPAC Systems, Santa Barbara, Calif.).

2. Identification of Correction Compounds

Typical protocol utilized a basolateral to apical membrane Cl⁻ concentration gradient. To set up this gradient, normal ringer was used on the basolateral membrane, whereas apical NaCl was replaced by equimolar sodium gluconate (titrated to pH 7.4 with NaOH) to give a large Cl⁻ concentration gradient across the epithelium. All experiments were performed with intact monolayers. To fully activate ΔF508-CFTR, forskolin (10 µM) and the PDE inhibitor, IBMX (100 µM), were applied followed by the addition of the CFTR potentiator, genistein (50 µM).

As observed in other cell types, incubation at low temperatures of FRT cells stably expressing ΔF508-CFTR increases the functional density of CFTR in the plasma membrane. To determine the activity of correction compounds, the cells were incubated with 10 µM of the test compound for 24 hours at 37° C. and were subsequently washed three times prior to recording. The cAMP- and genistein-mediated $I_{SC}$ in compound-treated cells was normalized to the 27° C. and 37° C. controls and expressed as percentage activity. Preincubation of the cells with the correction compound significantly increased the cAMP- and genistein-mediated $I_{SC}$ compared to the 37° C. controls.

3. Identification of Potentiator Compounds

Typical protocol utilized a basolateral to apical membrane Cl⁻ concentration gradient. To set up this gradient, normal ringers were used on the basolateral membrane and permeabilized with nystatin (360 µg/ml), whereas apical NaCl was replaced by equimolar sodium gluconate (titrated to pH 7.4 with NaOH) to give a large Cl⁻ concentration gradient across the epithelium. All experiments were performed 30 minutes after nystatin permeabilization. Forskolin (10 µM) and all test compounds were added to both sides of the cell culture inserts. The efficacy of the putative ΔF508-CFTR potentiators was compared to that of the known potentiator, genistein.

4. Solutions

Basolateral solution (in mM): NaCl (135), $CaCl_2$ (1.2), $MgCl_2$ (1.2), $K_2HPO_4$ (2.4), $KHPO_4$ (0.6), N-2-hydroxyethylpiperazine-N'-2-ethanesulfonic acid (HEPES) (10), and dextrose (10). The solution was titrated to pH 7.4 with NaOH.

Apical solution (in mM): Same as basolateral solution with NaCl replaced with Na Gluconate (135).

5. Cell Culture

Fisher rat epithelial (FRT) cells expressing ΔF508-CFTR ($FRT^{\Delta F508-CFTR}$) were used for Ussing chamber experiments for the putative ΔF508-CFTR modulators identified from our optical assays. The cells were cultured on Costar Snapwell cell culture inserts and cultured for five days at 37° C. and 5% $CO_2$ in Coon's modified Ham's F-12 medium supplemented with 5% fetal calf serum, 100 U/ml penicillin, and 100 µg/ml streptomycin. Prior to use for characterizing the potentiator activity of compounds, the cells were incubated at 27° C. for 16 to 48 hrs to correct for the ΔF508-CFTR. To determine the activity of corrections compounds, the cells were incubated at 27° C. or 37° C. with and without the compounds for 24 hours.

6. Whole-Cell Recordings

The macroscopic ΔF508-CFTR current ($I_{\Delta F508}$) in temperature- and test compound-corrected NIH3T3 cells stably expressing ΔF508-CFTR were monitored using the perforated-patch, whole-cell recording. Briefly, voltage-clamp recordings of $I_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5 to 6 MΩ when filled with the intracellular solution. Under these recording conditions, the calculated reversal potential for Cl⁻ ($E_{Cl}$) at room temperature was −28 mV. All recordings had a seal resistance greater than 20 GΩ and a series resistance less than 15 MΩ. Pulse generation, data acquisition, and analysis were performed using a PC equipped with a Digidata 1320 A/D interface in conjunction with Clampex 8 (Axon Instruments Inc.). The bath contained less than 250 µl of saline and was continuously perifused at a rate of 2 ml/min using a gravity-driven perfusion system.

7. Identification of Correction Compounds

To determine the activity of correction compounds for increasing the density of functional ΔF508-CFTR in the plasma membrane, the above-described perforated-patch-recording techniques were used to measure the current density following 24-hour treatment with the correction compounds. To fully activate ΔF508-CFTR, 10 μM forskolin and 20 μM genistein were added to the cells. Under our recording conditions, the current density following 24-hr incubation at 27° C. was higher than that observed following 24-hour incubation at 37° C. These results are consistent with the known effects of low-temperature incubation on the density of ΔF508-CFTR in the plasma membrane. To determine the effects of correction compounds on CFTR current density, the cells were incubated with 10 μM of the test compound for 24 hours at 37° C. and the current density was compared to the 27° C. and 37° C. controls (% activity). Prior to recording, the cells were washed three times with extracellular recording medium to remove any remaining test compound. Preincubation with 10 μM of correction compounds significantly increased the cAMP- and genistein-dependent current compared to the 37° C. controls.

8. Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

9. Solutions

Intracellular solution (in mM): Cs-aspartate (90), CsCl (50), $MgCl_2$ (1), HEPES (10), and 240 μg/ml amphotericin-B (pH adjusted to 7.35 with CsOH).

Extracellular solution (in mM): N-methyl-D-glucamine (NMDG)-Cl (150), $MgCl_2$ (2), $CaCl_2$ (2), and HEPES (10) (pH adjusted to 7.35 with HCl).

10. Cell Culture

NIH3T3 mouse fibroblasts stably expressing ΔF508-CFTR are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1×pen/strep, and 25 mM HEPES in 175 cm² culture flasks. For whole-cell recordings, 2,500-5,000 cells were seeded on poly-L-lysine-coated glass coverslips, cultured for 24 to 48 hours at 27° C. before use to test the activity of potentiators, and incubated with or without the correction compound at 37° C. for measuring the activity of correctors.

11. Single-Channel Recordings

The single-channel activities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5 to 8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1 to 2 seconds. To maintain ΔF508-CFTR activity during the rapid perifusion, the nonspecific phosphatase inhibitor F⁻ (10 mM NaF) was added to the bath solution. Under these recording conditions, channel activity remained constant throughout the duration of the patch recording (up to 60 minutes). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing ≤2 active channels. The maximum number of simultaneous openings determined the number of active channels during the course of an experiment. To determine the single-channel current amplitude, the data recorded from 120 seconds of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

12. Solutions

Extracellular solution (in mM): NMDG (150), aspartic acid (150), $CaCl_2$ (5), $MgCl_2$ (2), and HEPES (10) (pH adjusted to 7.35 with Tris base).

Intracellular solution (in mM): NMDG-Cl (150), $MgCl_2$ (2), EGTA (5), TES (10), and Tris base (14) (pH adjusted to 7.35 with HCl).

13. Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1×pen/strep, and 25 mM HEPES in 175 cm² culture flasks. For single channel recordings, 2,500-5,000 cells were seeded on poly-L-lysine-coated glass coverslips and cultured for 24-48 hrs at 27° C. before use.

Using the procedures described above, the activity, i.e., EC50s, of Compound 1 has been measured by the techniques above and is shown in Table 6.

TABLE 6

| IC50/EC50 Bins: +++ <= 2.0 < ++ <= 5.0 < + | | |
| PercentActivity Bins: + <= 25.0 < ++ <= 100.0 < +++ | | |
| Cmpd. No. | BinnedEC50 | BinnedMaxEfficacy |
| --- | --- | --- |
| 1 | +++ | +++ |

OTHER EMBODIMENTS

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and

We claim:

1. A solid form of 3-(6-(I-(2,2-Difluorobenzo[d][1,3]dioxol-5-yl)cyclopropanecarboxamido)-3-methylpyridin-2-yl)benzoic acid (Compound 1), characterized as Compound 1, Solvate Form A.

2. Compound 1, Solvate Form A of claim 1, wherein Compound 1, Solvate Form A is characterized as a crystalline lattice of Compound 1 containing a plurality of repeating cavities which are empty or at least partially occupied by a solvate.

3. Compound 1, Solvate Form A of claim 1, wherein Compound 1, Solvate Form A is characterized as a crystalline lattice of Compound 1 containing a plurality of repeating cavities, wherein a plurality of the cavities are empty.

4. Compound 1, Solvate Form A of claim 1, characterized by one or more peaks at 21.5 to 21.9 degrees, 8.8 to 9.2 degrees, and 10.8 to 11.2 degrees in an X-ray powder diffraction obtained using Cu K alpha radiation.

5. Compound 1, Solvate Form A of claim 1, characterized by one or more peaks at 21.5 to 21.9 degrees, 8.8 to 9.2 degrees, 10.8 to 11.2 degrees, 18.0 to 18.4 degrees, and 22.9 to 23.3 degrees in an X-ray powder diffraction obtained using Cu K alpha radiation.

6. Compound 1, Solvate Form A of claim 1, characterized by one or more peaks at 21.70, 8.98, 11.04, 18.16, and 23.06 degrees in an X-ray powder diffraction obtained using Cu K alpha radiation.

7. Compound 1, Solvate Form A of claim 1, characterized by a peak at 21.5 to 21.9 degrees in an X-ray powder diffraction obtained using Cu K alpha radiation.

8. Compound 1, Solvate Form A of claim 7, characterized by a peak at 21.70 degrees in an X-ray powder diffraction obtained using Cu K alpha radiation.

9. Compound 1, Solvate Form A of claim 7, further characterized by a peak at 8.8 to 9.2 degrees in an X-ray powder diffraction obtained using Cu K alpha radiation.

10. Compound 1, Solvate Form A of claim 9, further characterized by a peak at 8.98 degrees in an X-ray powder diffraction obtained using Cu K aloha radiation.

11. Compound 1, Solvate Form A of claim 9, further characterized by a peak at 10.8 to 11.2 degrees in an X-ray powder diffraction obtained using Cu K alpha radiation.

12. Compound 1, Solvate Form A of claim 11, further characterized by a peak at 11.04 in an X-ray powder diffraction obtained using Cu K alpha radiation.

13. Compound 1, Solvate Form A of claim 11, further characterized by a peak at 18.0 to 18.4 degrees in an X-ray powder diffraction obtained using Cu K alpha radiation.

14. Compound 1, Solvate Form A of claim 13, further characterized by a peak at 18.16 degrees in an X-ray powder diffraction obtained using Cu K aloha radiation.

15. Compound 1, Solvate Form A of claim 13, further characterized by a peak at 22.9 to 23.3 degrees in an X-ray powder diffraction obtained using Cu K alpha radiation.

16. Compound 1, Solvate Form A of claim 15, further characterized by a peak at 23.06 degrees in an X-ray powder diffraction obtained using Cu K alpha radiation.

17. Compound 1, Solvate Form A of claim 2, wherein the Compound 1, Solvate Form A is characterized by a diffraction pattern substantially similar to that of FIG. 1.

18. Compound 1, Solvate Form A of claim 2, wherein the solvent is selected from the group consisting of an organic solvent of sufficient size to fit in the plurality of repeating cavities.

19. Compound 1, Solvate Form A of claim 18, wherein the solvent is selected from the group consisting of methanol, ethanol, acetone, isopropanol, acetonitrile, tetrahydrofuran, methyl acetate, 2-butanone, ethyl formate, ethyl acetate, and 2-methyltetrahydrofuran.

20. Compound 1, Solvate Form A of claim 18, wherein Compound 1, Solvate Form A comprises 1 to 10 wt. % solvent as determined by TGA.

21. Compound 1, Solvate Form A of claim 2, wherein Compound 1, Solvate Form A comprises 2 to 5 wt. % solvent as determined by TGA.

22. Compound 1, Solvate Form A of claim 2, wherein the melting point is from 185° C. to 190° C.

23. Compound 1, Solvate Form A of claim 2, having a P2$_1$/n space group, and the following unit cell dimensions:
a=16.5235 (10) Å α=90°
b=12.7425 (8)Å β=103.736 (4) 0
c=20.5512 (13)Å γ=90°.

24. Compound 1, Solvate Form A of claim 1, wherein Compound 1, Solvate Form A has a particle size of 0.1 microns to 50 microns.

25. Compound 1, Solvate Form A of claim 1, wherein Compound 1, Solvate Form A has a particle size of 0.1 microns to 20 microns.

26. Compound 1, Solvate Form A of claim 1, wherein Compound 1, Solvate Form A has a particle size of 0.1 microns to 10 microns.

27. Compound 1, Solvate Form A of claim 1, wherein Compound 1, Solvate Form A has a particle size of 1.0 microns to 5 microns.

28. Compound 1, Solvate Form A, wherein Compound 1, Solvate Form A has a particle size D50 of 2.0 microns.

29. A pharmaceutical composition comprising Compound 1, Solvate Form A of claim 1, and a pharmaceutically acceptable carrier.

30. The pharmaceutical composition of claim 29 further comprising an additional therapeutic agent.

31. A method of treating a CFTR mediated disease in a mammal comprising administering to the mammal an effective amount of Compound 1, Solvate Form A of claim 1, wherein the CFTR mediated disease is selected from chloride channelopathies, COPD, asthma, cystic fibrosis, male infertility caused by congenital bilateral absence of the vas deferens, pancreatitis, pancreatic insufficiency, and idiopathic pancreatitis.

32. The method of claim 31, wherein the CFTR mediated disease is cystic fibrosis or COPD.

33. The method of claim 32, wherein the CFTR mediated disease is cystic fibrosis.

34. The method of claim 32, wherein said patient has a cystic fibrosis transmembrane receptor (CFTR) with a ΔF508 mutation.

35. The method of claim 32, wherein said patient has a cystic fibrosis transmembrane receptor (CFTR) with a R117H mutation.

36. The method of claim 32, wherein said patient has a cystic fibrosis transmembrane receptor (CFTR) with a G551 D mutation.

37. The method of claim 31, wherein the method further comprises administering an additional therapeutic agent which is N-(5-hydroxy-2,4-ditert-butyl-phenyl)-4-oxo-1H-quinoline-3-carboxamide.

* * * * *